(12) United States Patent
Eror et al.

(10) Patent No.: US 10,117,596 B2
(45) Date of Patent: Nov. 6, 2018

(54) METHOD FOR DIAGNOSING A MALIGNANT LUNG TUMOR

(71) Applicant: Fresh Medical Laboratories, Inc., Salt Lake City, UT (US)

(72) Inventors: Steven C Eror, Salt Lake City, UT (US); Michael A Garff, Salt Lake City, UT (US)

(73) Assignee: PROLUNG, INC., Salt Lake City, UT (US)

( * ) Notice: Subject to any disclaimer, the term of this patent is extended or adjusted under 35 U.S.C. 154(b) by 297 days.

(21) Appl. No.: 13/970,496

(22) Filed: Aug. 19, 2013

(65) Prior Publication Data

US 2015/0051504 A1 Feb. 19, 2015

(51) Int. Cl.
| | | |
|---|---|---|
| *A61B 5/053* | (2006.01) | |
| *A61B 5/085* | (2006.01) | |
| *A61B 5/08* | (2006.01) | |
| *G06F 19/00* | (2018.01) | |
| *A61B 5/00* | (2006.01) | |

(52) U.S. Cl.
CPC .............. *A61B 5/053* (2013.01); *A61B 5/08* (2013.01); *A61B 5/085* (2013.01); *A61B 5/7264* (2013.01); *G06F 19/00* (2013.01); *A61B 5/7221* (2013.01)

(58) Field of Classification Search
CPC ..... A61B 5/053; A61B 5/0537; A61B 5/0536; A61B 5/085; A61B 2018/00541; G06K 2209/05; G06K 2209/051; G06K 2209/053
USPC ........................................................ 600/547
See application file for complete search history.

(56) References Cited

U.S. PATENT DOCUMENTS

| | | |
|---|---|---|
| 5,386,720 A | 2/1995 | Toda et al. |
| 7,603,171 B2 | 10/2009 | Eror et al. |
| 8,121,677 B2 | 2/2012 | Eror et al. |
| 2002/0146371 A1* | 10/2002 | Li ................. A61K 49/0004 424/1.73 |
| 2002/0183645 A1 | 12/2002 | Nachaliel |
| 2004/0204658 A1 | 10/2004 | Dietz et al. |
| 2005/0015017 A1 | 1/2005 | Horne et al. |
| 2006/0020223 A1 | 1/2006 | Horne et al. |
| 2007/0239061 A1 | 10/2007 | Carter et al. |
| 2010/0094160 A1 | 4/2010 | Eror et al. |
| 2011/0289035 A1* | 11/2011 | Stojadinovic ........... G06F 19/24 706/45 |

OTHER PUBLICATIONS

Nolte, et al. "Chemical and physiochemical comparison of advanced atherosclerotic lesions of similar size . . ." Laboratory investigation; a journal of technical methods and pathology 62.2 (1990): Abstract. Retrieved from <http://europepmc.org/abstract/med/2304334>.*

(Continued)

*Primary Examiner* — David J McCrosky
(74) *Attorney, Agent, or Firm* — Kunzler, PC

(57) ABSTRACT

A method to determine presence of a disease condition in a medical patient by evaluating conductivity information. Point-attributes values obtained from highly accurate conductivity data-sets taken as a function of time, over a period of time, are compared to previously determined threshold values. Z-scores may be determined to combine a plurality of point-attribute values in formulation of a composite score for a patient. Sometimes, z-scores are weighted by overall accuracy of the point-attribute in predicting presence of the disease.

10 Claims, 4 Drawing Sheets

(56) References Cited

OTHER PUBLICATIONS

Hodges, Jr. et al. (2005). Basic Concepts of Probability and Statistics (2nd Edition). Society for Industrial and Applied Mathematics. Retrieved from <http://app.knovel.com/hotlink/toc/id:kpBCPSE008/basic-concepts-probability/basic-concepts-probability> on Jun. 27, 2017.*

Reeves, "The Lung Image Database Consortium (LIDC): a comparison of different size metrics for pulmonary nodule measurements." Academic radiology 14.12 (2007): Abstract.*

Internet Archive, Castillo. "Stratified Sampling Method." Explorable.com. Feb 20, 2013. Retrieved from <https://web.archive.org/web/20130220104527/https://explorable.com/stratified-sampling> on Jun. 27, 2017.*

Patz, Jr., et al. "Correlation of tumor size and survival in patients with stage IA non-small cell lung cancer." CHEST Journal 117.6 (2000): Abstract.*

Brown, Brian, et al., Detection of cervical intraepithelial neoplasia using impedance spectroscopy: a prospective study, BJOG: An International Journal of Obstetrics and Gynaecology, Jun. 2005, vol. 112, pp. 802-806.

Toso, Silvia, et al., Altered Tissue Electric Properties in Lung Cancer Patients as Detected by Bioelectric Impedance Vector Analysis, Basic Nutritional Investigation, 16: 120-124, 2000.

Alpert, Susan. FDA Approval Letter for TransScan, Apr. 16, 1999.

Toso, Silvia. Bioimpedance Vector Pattern in Cancer Patients Without Disease Versus Locally Advanced or Disseminated Disease, Applied Nutritional Investigation, 19:510-514, 2003.

Swensen, Stephen J. et al., CT Screening for Lung Cancer: Five-Year Prospective Experience, Radiology, Apr. 2005, pp. 259-265, vol. 235 No. 1.

Gupta, Digant, Bioelectrical impedance phase angle as a prognostic indicator in breast cancer, BMC Cancer: 2008, 8:249.

Flehinger, B.J., et al., The effect of surgical treatment on survival from early lung cancer. Implications for screening, Chest, 1992, 101:1013-1018, Apr. 1992.

Nesbitt, Jonathan, et al., Survival in early stage, non-small cell lung cancer, Ann. Thor. Surg. 1995, 60:466-472.

Shah, Rajesh, et al., Results of surgical treatment of stage I and stage II lung cancer, J. Cardiovascular Surgery, 1996, 37: 169-172.

Schwan, Herman P. The practical success of impedance techniques from an historical perspective, Annals New York Academy of Sciences, 1999; 873: 1-12.

Stojadinovic A, Nissan A, Gallimidi Z et al. Electrical Impedance scanning for the early detection of breast cancer in young women: preliminary results of a multicenter prospective clinical trial. J Clin Oncol2005; 23 (12): 2703-2715.

Cherepenin Y, Karpov A, KorjenevskyA et al. Preliminary static EIT images of the thorax in health and disease. Physiol Meas 2002; 23: 33-41.

Aberg P, Nicander I, Hansson J et al. Skin cancer identification using multifrequency electrical impedance—a potential screening tool. IEEE Trans Biomed Eng 2004; 51 (12): 2097-2102.

Malich A, Boehm T, Facius M et al. Use of electrical impendance scanning in the differentation of sonographically suspicious and highly suspicious lymph nodes of the head-neck region. Eur Radiol 2002; 12 (5): 1114-1120.

Mentzel HJ, Malich A, Kentouche K et al. Electrical impedance scanning-application of this new technique for lymph node evaluation in children. Pediatr Radio12003; 33 (7): 461-466.

Stojadinovic A, Fields SI, Shriver CD et al. Electrical impedance scanning of thyroid nodules before thyroid surgery: a prospective study. Ann Surg Oncol2005; 12 (2): 152-160.

Malich A, Boehm T, Facius M et al. Additional value of electrical impedance scanning: experience of 240 histologically-proven breast lesions. Eur J Cancer 2001; 37(18): 2324-2330.

* cited by examiner

METHOD FOR DIAGNOSING A MALIGNANT LUNG TUMOR

FIELD OF INVENTION

This invention relates generally to diagnosis of a disease condition in a mammal. It is particularly directed to detecting malignant lung cancer in a human by evaluating bioelectrical measurements taken between discreet points on the subject human body.

BACKGROUND

Electrical impedance is the ratio of the voltage difference to the current across a circuit or a body (Ohm's law), and conductance is the inverse of impedance (1/impedance). The dielectric properties of human cells and tissue are widely recognized and are essential for several diagnostic procedures currently in use. The Coulter Counter for electronic cell counting, the electrocardiogram for assessing cardiac functioning, and the encephalogram for evaluating brain functioning are some common examples.

The dielectric properties of the human body are well-characterized in literature and provide the basis for several clinical tests including electrocardiography, electroencephalography, plethysmography, electrical conductance tomography and BIA. Moreover, there is clear evidence that cancerous tissues differ in their bioelectrical conductance properties compared to those of benign and adipose tissue, and a device using bioelectrical conductance measurements has been approved by the United States Food and Drug Agency for use as a diagnostic adjunctive to mammography in the work-up of breast cancer in women under 40 years of age. The same technology is currently being evaluated as a screening test. Investigations have also been conducted for various other malignancies including cervical, skin, lymph nodes, thyroid, and lung cancer. In the bioelectrical assessment of lung cancer, there is evidence that electrical impedance tomography is capable of imaging the lungs, however limited information exists concerning the most effective access points and the modalities for bioelectrical conductivity measurement.

Many clinical investigations have examined the potential of using electrical properties for aiding in cancer diagnosis. Aberg and colleagues reported on the use of electrical bio-conductance to assess skin cancers. They found separation of malignant melanoma and non-melanoma skin cancer from benign nevi with 75% and 87% specificity, respectively, and 100% sensitivity for both. This was considered equal to, or better than, conventional visual screening. Electrical conductance scanning also shows promise in lymph node evaluation in children and adults. Malich et al reported that of 106 sonographically suspicious lymph nodes in the head and neck region, electrical conductance scanning was able to detect 62 of 64 malignant nodes for a true positive rate of 96.9%. However in this study, only 19 of 42 inflammatory benign lymph nodes were correctly identified as benign for a true negative rate of 45.2%. The authors conclude that while these results are promising, further development work is needed to reduce the high number of false-positives. Similar results were reported when potentially malignant lymph nodes were evaluated in children using electrical conductance. Another recent prospective study of electrical conductance scanning of 64 patients who were undergoing surgery for possible thyroid malignancies found that it is a potentially useful imaging modality for differentiating thyroid neoplasms.

Breast cancer has probably been studied the most extensively with conductance technology. Investigations of electrical conductance scanning in patients with sonographically or mammographically suspicious lesions found that there were significant differences between the tissues of normal and abnormal subjects. By considering electrical conductance results in addition to ultrasound and mammography, the sensitivity of cancer detection increased from 86% to 95%. In 1999, the US FDA approved a multi-frequency conductance breast scanner (T-Scan 2000) for use as an adjunct to mammography for select patients. A recent study of the T-Scan 2000ED which used a modified algorithm provided preliminary evidence that electrical conductance scanning might be valuable for early detection of breast cancer in young women at increased risk for having disease at the time of scanning.

Other recent investigations have shown that conductance spectroscopy may be a viable screening tool for detection of cervical cancer. Additional studies in humans demonstrated altered electrical properties in tissues of patients with various cancers including lung, pancreas and colorectal compared to those without cancer. Several of these studies have been done in lung cancer patients providing evidence that alterations in bioelectrical conductance are evident in this patient population.

Although there is clear evidence that survival is increased by resection and oncolytic intervention of earlier stage lung cancer, detection at the earlier stages remains difficult. The current interest and ongoing investigation of using low-dose CT scanning for screening presents challenges as well. It is almost universally agreed that CT scanning of high risk subjects identifies nodules that qualify for further clinical evaluation, either by repeat CT scan or biopsy, and yet 92-96% of identified lesions will be found to be benign. As a result, the economic and health costs associated with using CT scan in this modality is not offset by clinical benefit.

Consequently, there is a long felt need for a non-significant risk, non-invasive technology that could be utilized in conjunction with CT scanning to further differentiate suspicious masses or nodules identified by CT. Such differentiating information desirably would be clinically meaningful in identifying which patients should proceed for further diagnostic evaluation and those that are likely to have a benign finding.

SUMMARY OF THE INVENTION

This present invention relates to methods for diagnosing lung cancer in a medical patient.

In one aspect, the invention relates to a method to effectively discriminate between having a malignant lung lesion and not having a malignant lung lesion in a medical patient, comprising:

- providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;
- measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values; and comparing a plurality of curve attribute values obtained from the at least one patient data set to a plurality of corresponding curve attribute values in a previously-determined corresponding data set obtained using a similar measuring step;

wherein the previously-determined corresponding data set was determined by comparing, from a population of patients having lung lesions, (i) a first cohort having malignant lung lesions and (ii) a second cohort not having malignant lung lesions, the malignant lung lesions of the previously-determined corresponding data set being determined by examination of lesion biopsies, to obtain a data set that effectively discriminates between the cohort having the malignant lung lesion and the cohort not having a malignant lung lesion, to thereby determine the likelihood of the patient having a malignant lung lesion.

In some embodiments, the at least one value in a previously-determined corresponding data set comprises a threshold value indicative of a likelihood of the patient having a malignant lesion. In other embodiments, the previously determined data set provides threshold values for a plurality of point-attributes that satisfy a threshold criteria of ROC area sufficient to discriminate between a patient having a malignant lung lesion and a patient not having a malignant lung lesion. In still other embodiments, the threshold values for the plurality of point-attributes satisfy a threshold criteria of greater than about 70% ROC area for discriminating between a patient having a malignant lung lesion and a patient not having a malignant lung lesion.

In another aspect, in the methods of the present invention, the previously determined corresponding data set is derived from a population of patients having lung lesions located in a similar region of the lung as the lesion in the patient. In some embodiments, the lung lesion of the patient is present in a lung location selected from one or more of the right lobe (RL) and the left lobe (LL), and the previously determined corresponding data set is obtained from a cohort having malignant lung lesions and a cohort having benign lung lesions in a similar region of the lung. In some embodiments, the lung lesion of the patient is present in a lung location selected from one or more of the right lower lobe (RLL), right middle lobe (RML), right upper lobe (RUL), left lower lobe (LLL), and left upper lobe (LUL), and the previously determined corresponding data set is obtained from a cohort having malignant lung lesions and a cohort having benign lung lesions in a similar region of the lung. In other embodiments, the lung lesion of the patient is of a size similar to the size of the lung lesions used to obtain the previously determined corresponding data set. In yet other embodiments, the lung lesions of the patient and the lung lesions used to obtain the previously determined corresponding data set range in size from 0 to about 15 mm, about 16 to about 30 mm, or from about 31 mm or greater.

In other embodiments, the lung lesions of the patient and the lung lesions used to obtain the previously determined corresponding data set differ in size by no greater than about 2 mm, 5 mm, 10 mm, or 15 mm.

In another aspect of the invention, the point-attribute values comprise the total number of points measured to form the curve. In some embodiments, the point attribute values comprise an area under the curve (AUC) measurement calculated by measuring the area under the curve of a plot of the conductivity index over time of a curve segment from the point at which the slope of the curve is stable. In other embodiments, the point attribute values comprise an area under the curve (AUC) measurement calculated by measuring the area under the curve of a plot of the conductivity index over time of a curve segment from the point at which the slope of the curve is stable, wherein the duration of the curve segment comprises at least 5 seconds. In yet other embodiments, the point attribute values further comprise an area under the curve (AUC) measurement calculated by measuring the area under the curve of a plot of the conductivity index over time of a curve segment comprising the last 5 seconds of the curve.

In another aspect, the point-attribute values comprise an area under the curve (AUC) measurement calculated by measuring the height of the curve at selected intervals and summing said heights. In some embodiments, the height of the curve is calculated at intervals of about 25× per second.

In some aspects, the methods comprise developing a composite score for a patient indicative of a likelihood of the patient having lung cancer. In other aspects, the methods comprise a composite score that is developed by converting a subset of obtained point-attribute values to corresponding z-scores, and combining the z-scores.

In another aspect, the present invention relates to methods to effectively discriminate between having a malignant lung lesion and not having a malignant lung lesion in a medical patient, comprising:

providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;

measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;

comparing a plurality of curve attribute values obtained from the at least one patient data set to a plurality of corresponding curve attribute values in a previously-determined corresponding data set obtained using a similar measuring step, wherein at least one of the curve attribute values is the total number of points measured to form the curve;

wherein the previously-determined corresponding data set was determined by comparing, from a population of patients having lung lesions, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

In another aspect, the present invention relates to methods to effectively discriminate between having a malignant lung lesion and not having a malignant lung lesion in a medical patient, comprising:

providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;

measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;

comparing a plurality of curve attribute values obtained from the at least one patient data set to a plurality of corresponding curve attribute values in a previously-determined corresponding data set obtained using a similar measuring step;

wherein the previously-determined corresponding data set was determined by comparing, from a population of patients having lung lesions located in a similar region of the lung as the lesion of the patient, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

In some embodiments, the lung lesion of the patient is present in a region of the lung selected from one or more of the right lobe (RL) and the left lobe (LL), and the previously determined corresponding data set is obtained from a cohort having malignant lung lesions and a cohort having benign lung lesions in the same lung location. In some embodiments, the lung lesion of the patient is present in a region of the lung selected from one or more of the right lower lobe (RLL), right middle lobe (RML), right upper lobe (RUL), left lower lobe (LLL), and left upper lobe (LUL), and the previously determined corresponding data set is obtained from a cohort having malignant lung lesions and a cohort having benign lung lesions in the same lung location.

In another aspect, the present invention relates to a method to effectively discriminate between having a malignant lung lesion and not having a malignant lung lesion in a medical patient, comprising:

providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;

measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;

comparing a plurality of curve attribute values obtained from the at least one patient data set to a plurality of corresponding curve attribute values in a previously-determined corresponding data set obtained using a similar measuring step;

wherein the previously-determined corresponding data set was determined by comparing, from a population of patients having lung lesions of similar size as the lung lesion of the patient, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

In another aspect, the present invention relates to a method to effectively discriminate between having a malignant lung lesion and not having a malignant lung lesion in a medical patient, comprising:

providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;

measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;

comparing a plurality of curve attribute values obtained from the at least one patient data set to a plurality of corresponding curve attribute values in a previously-determined corresponding data set obtained using a similar measuring step, wherein the point attribute values comprise an area under the curve (AUC) measurement calculated by measuring the area under the curve of a plot of the conductivity index over time of a curve segment from the point at which the slope of the curve is stable;

wherein the previously-determined corresponding data set was determined by comparing, from a population of patients having lung lesions, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

BRIEF DESCRIPTION OF THE DRAWINGS

The following drawings illustrate what are currently considered to be specific embodiments for carrying out the invention.

DETAILED DESCRIPTION

Figure 1:
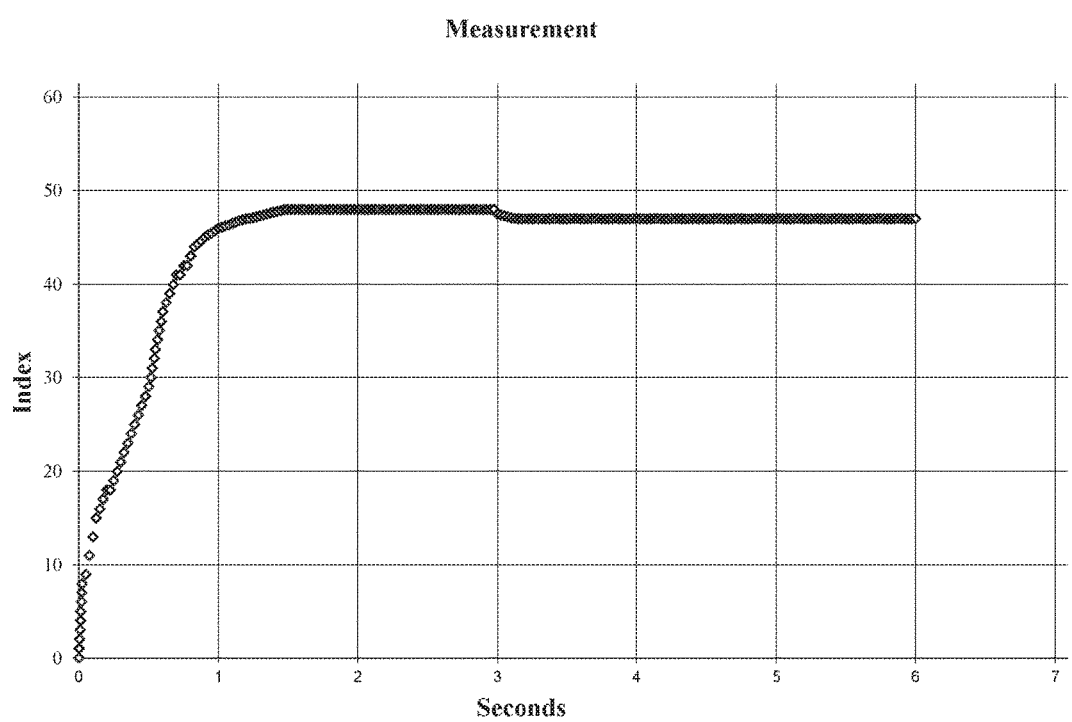
FIG. 1 is a representative plot of a conductivity data-set obtained during measurement of conductivity between a first point and a second point on the surface of a medical patient.

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

The device used to practice the currently preferred embodiments of the invention is shown generally in U.S. Pat. No. 8,121,677 (the contents of which are incorporated herein, in its entirety), which is operable in practice of a method according to certain principles of the instant invention. The device includes a computer assembly, and a probe system. The computer assembly typically includes a housing to contain a processor and memory in communication with a display device, such as monitor. One or more input device, such as a keyboard, a mouse, or the like, may also be included in operable association with the computer assembly. Similarly, an output device, such as a printer, USB port, network connector, media writer, and the like, may be disposed in operable relation with a computer system.

The probe system typically includes an interrogation electrode. A currently preferred interrogation electrode is disclosed in U.S. Pat. No. 8,121,677. Desirably, an interrogation electrode will be structured to permit computer controlled application of electrode contact pressure force onto a subject's skin during a measurement sequence. Such computer control desirably includes a feedback loop encompassing real-time conductivity data as measured by the probe itself.

Probe system also includes a reference electrode. Suitable reference electrodes may comprise a hand-held metal cylindrical electrode that is held in the hand of a subject, or a spot probe that may be applied by the clinician. Another type of suitable electrode for use as a reference electrode is an ECG monitoring electrode (ConMed Corporation, Utica, N.Y.). Such electrodes come conveniently in the form of a pre-gelled, single patient use, disposable electrocardiographic electrode for use an accessory to ECG equipment for long term or short term monitoring and diagnostic procedures. Such electrodes may have regular or diaphoretic adhesives. Desirably, the reference electrodes are structured to contact a relatively larger area of a measured subject's skin, and isolate the operator from the formed electrical circuit. The electrodes are placed into electrical communication with conductivity measuring equipment that may conveniently be contained in a housing for communication of electrical conductivity data to the computer system. The diaphoretic electrode is applied and the operator moves the electrode cable "snap" when prompted by the computer screen.

Data acquisition includes measuring conductivity as a function of time, and over a period of time, between a reference electrode disposed at one or more reference point, and an interrogation electrode disposed, typically, at each of a plurality of interrogation points. Certain interrogation point locations that may be operable for use in detecting lung cancer are located on the arms, hands, shoulder, chest, and back, as described below and are listed in the following table.

| Measurement Sequence | Data Acquisition Point |
| --- | --- |
| 1 | FML-1aTR |
| 2 | FML-1bTR |
| 3 | FML-1cTR |
| 4 | FML-2aTR |
| 5 | FML-1R |
| 6 | FML-2aR |
| 7 | FML-2bR |
| 8 | FML-2cR |
| 9 | FML-3aR |
| 10 | FML-3bR |
| 11 | FML-4R |
| 12 | FML-5R |
| 13 | FML-6aR |
| 14 | FML-6dR |
| 15 | FML-6eR |
| 16 | FML-7aR |
| 17 | FML-7bR |
| 18 | FML-7cR |
| 19 | FML-8aR |
| 20 | FML-8bR |
| 21 | FML-8cR |
| 22 | FML-8dR |
| 23 | FML-8eR |
| 24 | FML-8fR |
| 25 | FML-9R |
| 26 | FML-10R |
| 27 | FML-11aR |
| 28 | FML-11bR |
| 29 | FML-12aR |
| 30 | FML-12bR |
| 31 | FML-12cR |
| 32 | FML-1aTL |
| 33 | FML-1bTL |
| 34 | FML-1cTL |
| 35 | FML-2aTL |
| 36 | FML-1L |
| 37 | FML-2aL |
| 38 | FML-2bL |
| 39 | FML-2cL |
| 40 | FML-3aL |
| 41 | FML-3bL |
| 42 | FML-4L |
| 43 | FML-5L |
| 44 | FML-6aL |
| 45 | FML-6dL |
| 46 | FML-6eL |
| 47 | FML-7aL |
| 48 | FML-7bL |
| 49 | FML-7c8aLL |
| 50 | FML-8bL |
| 51 | FML-8cL |
| 52 | FML-8dL |
| 53 | FML-8eL |
| 54 | FML-8fL |
| 55 | FML-9L |
| 56 | FML-10L |
| 57 | FML- |
| 58 | FML-11aL |
| 59 | FML-11bL |
| 60 | FML-12aL |
| 61 | FML-12bL |
| 62 | FML-12cL |

Typically, the reference electrode will be placed on the top of the subject's hand on an opposite side of the body midline from the interrogation point during data acquisition for detection of lung cancer. That is, in such case, and for interrogation points having a label ending with "R", the reference electrode will be placed on the subject's left hand, and vice versa. Exceptions to this generalization are indicated in the following detailed descriptions of point locations.

FML-1 R is located between costa 3 and costa 4 at 1.5 thumb-widths lateral to the midpoint between the spinous process of the second and third thoracic vertebra.

FML-1aTR is located on the 2nd rib approximately 2½ thumb-width lateral from the midline or depression point on the sternum. NOTE: Use the reference electrode placed at FML-1 R.

FML-1 bTR is located in the 2nd intercostal space on a line between the lateral insertion of the sternocleidomastoid muscle and the nipple. It is approximately 3-3½ thumb-width from the midline. NOTE: Use the reference electrode placed at FML-1 R.

FML-1cTR is located in the 3rd intercostal space approximately 3½ thumb-width lateral from the midline. NOTE: Use the reference electrode placed at FML-1R.

FML-2aTR is located in the depression on the lower border of the clavicle, 2 thumb-widths lateral to the midline. The 2 thumb-width line is located midway between the midline and the mamillary line. Use the round reference electrode and place it 2 thumb-widths lateral to the midline of the spine on the back in the lowest intercostal space.

FML-2aR is located in the depression on the lower border of the clavicle, 2 thumb-widths lateral to the midline. The 2 thumb-width line is located midway between the midline and the mamillary line.

FML-2bR is located on the lateral aspect of the chest, in the first intercostal space, 6 thumb-widths lateral to the midline, 1 thumb-width inferior to FML-2c.

FML-2cR is located on the antero-lateral aspect of the chest, below the lateral extremity of the clavicle, 6 thumb-widths lateral to the midline, in the center of the hollow of the delto-pectoral triangle. Ask the patient to extend their hand forwards while you apply resistance to their hand, in order to emphasize the delto-pectoral triangle, and locate FML-2c at its center.

FML-3aR is located on the antero-lateral aspect of the upper arm, 3 thumb-widths inferior to the axillary fold and 6 thumb-widths superior to FML-4, in the depression between the lateral border of the biceps brachii muscle and the shaft of the humerus.

Divide the distance between the axillary fold and the cubital crease of the elbow into equal thirds. FML-3a is at the junction of the upper and middle third.

FML-3bR is located on the antero-lateral aspect of the upper arm, 4 thumb-widths inferior to the axillary fold and 5 thumb-widths superior to FML-4, in the depression between the lateral border of the biceps brachii muscle and the shaft of the humerus.

FML-4R is located on the cubital crease of the elbow, in the depression at the radial side of the tendon of biceps brachii.

FML-5R is located by moving from the wrist up the forearm along the flexor carpi radialis to the point where the brachioradialis is encountered.

FML-6aR is located on the radial artery, approximately 2½ inches above the wrist crease or 1 inch above the beginning of the styloid process of the radius bone. It is at the junction formed by the tendon of the brachioradialis and the flexor digitirum superficialis muscles.

FML-6dR is located approximately 1 inch proximal from the distal transverse wrist crease on the medial edge of the styloid process of the radius (palmar aspect of the hand).

FML-6eR is located at the lateral end of the distal wrist crease at the base of the palm. It is directly proximal to the lateral edge of the scaphoid's tubercle.

FML-7aR is located between the scaphoid and trapezium bones directly distal to the tubercle of the scaphoid.

FML-7bR is located at the proximal diaphyseal end of the first metacarpal bone, palmar aspect of the hand.

FML-7cR is located at the distal diaphyseal end of the 1st metacarpal bone on its ulnar side (palmar surface of the hand).

FML-8aR is located between the radius and navicular bones on the ulnar side of the extensor pollicis longus tendon.

FML-8bR is located at the distal diaphyseal end of the proximal phalanx of the thumb on its radial side. It is measured on a 45 degree angle with the probe pointing distally.

FML-8cR is located at the proximal diaphyseal end of the metacarpal phalanx of the thumb on its ulnar side (dorsal aspect of the hand). It is measured on a 45-degree angle with the probe pointing proximally.

FML-8dR is located at the distal diaphyseal end of the basal (proximal) phalanx of the thumb on its ulnar side (dorsal aspect of the hand). It is measured on a 45-degree angle with the probe pointing distally.

FML-8eR is located at the proximal diaphyseal end of the distal phalanx of the thumb (dorsal aspect). It is measured on a 45-degree angle with the probe pointing proximally.

FML-8fR is located at the distal diaphyseal end of the nail phalanx of the thumb on its ulnar side. It is measured on a 90-degree angle on the side of the finger with the probe on a horizontal plane with that of the fingernail.

FML-9R is located at the proximal diaphyseal end of the middle phalanx of the second finger on its ulnar side (dorsal aspect of the hand). It is measured on a 45 degree angle with the probe pointing proximally.

FML-10R is located at the proximal diaphyseal end of the middle phalanx of the 3rd finger on its radial side (dorsal aspect of the hand). It is measured on a 45 degree angle with the probe pointing proximally.

FML-11aR is located at the distal diaphyseal end of the ungual phalanx of the 4th finger on its ulnar side (dorsal aspect of the hand). It is measured on a 90 degree angle on the side of the finger.

FML-11bR is located at the proximal diaphyseal end of the middle phalanx of the 4th finger on its ulnar side (dorsal aspect of the hand). It is measured on a 45 degree angle with the probe pointing proximally.

FML-12aR is located at the distal diaphyseal end of the proximal phalanx of the little (5th) finger on its radial side (dorsal aspect of the hand). It is measured on a 45 degree angle with the probe pointing distally.

FML-12bR is located at the proximal diaphyseal end of the basal phalanx of the 5th finger on its ulnar side. It is measured on a 45 degree angle with the probe pointing proximally.

FML-12cR is located at the distal diaphyseal end of the nail phalanx of the 5th finger on its ulnar side (dorsal aspect of the hand). It is measured on a 90 degree angle on the side of the finger with the probe on a horizontal plane with that of the fingernail.

FML-1L is located between costa 3 and costa 4 at 1.5 thumb-widths lateral to the midpoint between the spinous process of the second and third thoracic vertebra.

FML-1aTL is located on the 2nd rib approximately 2½ thumb-width lateral from the midline or depression point on the sternum. NOTE: Use the reference electrode placed it at FML-1L.

FML-1 bTL is located in the 2nd intercostal space on a line between the lateral insertion of the sternocleidomastoid muscle and the nipple. It is approximately 3-3½ thumb-width from the midline. Use the reference electrode placed it at FML-1L.

FML-1cTL is located in the 3rd intercostal space approximately 3½ thumb-width lateral from the midline. Use the reference electrode placed at FML-1L.

FML-2aTL is located in the depression on the lower border of the clavicle, 2 thumb-widths lateral to the midline. The 2 thumb-width line is located midway between the midline and the mamillary line. Use the reference electrode and place it 2 thumb-widths lateral to the midline of the spine on the back in the lowest intercostal space.

FML-2aL is located in the depression on the lower border of the clavicle, 2 thumb-widths lateral to the midline. The 2 thumb-width line is located midway between the midline and the mamillary line.

FML-2bL is located on the lateral aspect of the chest, in the first intercostal space, 6 thumb-widths lateral to the midline, 1 thumb-width inferior to FML-2c.

FML-2cL is located on the antero-lateral aspect of the chest, below the lateral extremity of the clavicle, 6 thumb-widths lateral to the midline, in the center of the hollow of the delto-pectoral triangle. Ask the patient to extend their hand forwards while you apply resistance to their hand, in order to emphasize the delto-pectoral triangle, and locate FML-2c at its center.

FML-3aL is located on the antero-lateral aspect of the upper arm, 3 thumb-widths inferior to the axillary fold and 6 thumb-widths superior to FML-4, in the depression between the lateral border of the biceps brachii muscle and the shaft of the humerus.

Divide the distance between the axillary fold and the cubital crease of the elbow into equal thirds. FML-3a is at the junction of the upper and middle third.

FML-3bL is located on the antero-lateral aspect of the upper arm, 4 thumb-widths inferior to the axillary fold and 5 thumb-widths superior to FML-4, in the depression between the lateral border of the biceps brachii muscle and the shaft of the humerus.

FML-4L is located on the cubital crease of the elbow, in the depression at the radial side of the tendon of biceps brachii.

FML-5L is located by moving from the wrist up the forearm along the flexor carpi radialis to the point where the brachioradialis is encountered.

FML-6aL is located on the radial artery, approximately 2½ inches above the wrist crease or 1 inch above the beginning of the styloid process of the radius bone. It is at the junction formed by the tendon of the brachioradialis and the flexor digitirum superficialis muscles.

FML-6dL is located approximately 1 inch proximal from the distal transverse wrist crease on the medial edge of the styloid process of the radius (palmar aspect of the hand).

FML-6eL is located at the lateral end of the distal wrist crease at the base of the palm. It is directly proximal to the lateral edge of the scaphoid's tubercle.

FML-7aL is located between the scaphoid and trapezium bones directly distal to the tubercle of the scaphoid.

FML-7bL is located at the proximal diaphyseal end of the first metacarpal bone, palmar aspect of the hand.

FML-7cL is located at the distal diaphyseal end of the 1st metacarpal bone on its ulnar side (palmar surface of the hand).

FML-8aL is located between the radius and navicular bones on the ulnar side of the extensor pollicis longus tendon.

FML-8bL is located at the distal diaphyseal end of the proximal phalanx of the thumb on its radial side. It is measured on a 45 degree angle with the probe pointing distally.

FML-8cL is located at the proximal diaphyseal end of the metacarpal phalanx of the thumb on its ulnar side (dorsal aspect of the hand). It is measured on a 45-degree angle with the probe pointing proximally.

FML-8dL is located at the distal diaphyseal end of the basal (proximal) phalanx of the thumb on its ulnar side (dorsal aspect of the hand). It is measured on a 45-degree angle with the probe pointing distally.

FML-8eL is located at the proximal diaphyseal end of the distal phalanx of the thumb (dorsal aspect). It is measured on a 45-degree angle with the probe pointing proximally.

FML-8fL is located at the distal diaphyseal end of the nail phalanx of the thumb on its ulnar side. It is measured on a 90-degree angle on the side of the finger with the probe on a horizontal plane with that of the fingernail.

FML-9L is located at the proximal diaphyseal end of the middle phalanx of the second finger on its ulnar side (dorsal aspect of the hand). It is measured on a 45 degree angle with the probe pointing proximally.

FML-10L is located at the proximal diaphyseal end of the middle phalanx of the 3rd finger on its radial side (dorsal aspect of the hand). It is measured on a 45 degree angle with the probe pointing proximally.

FML-11aL is located at the distal diaphyseal end of the ungual phalanx of the 4th finger on its ulnar side (dorsal aspect of the hand). It is measured on a 90 degree angle on the side of the finger.

FML-11bL is located at the proximal diaphyseal end of the middle phalanx of the 4th finger on its ulnar side (dorsal aspect of the hand). It is measured on a 45 degree angle with the probe pointing proximally.

FML-12aL is located at the distal diaphyseal end of the proximal phalanx of the little (5th) finger on its radial side (dorsal aspect of the hand). It is measured on a 45 degree angle with the probe pointing distally.

FML-12bL is located at the proximal diaphyseal end of the basal phalanx of the 5th finger on its ulnar side. It is measured on a 45 degree angle with the probe pointing proximally.

FML-12cL is located at the distal diaphyseal end of the nail phalanx of the 5th finger on its ulnar side (dorsal aspect of the hand). It is measured on a 90 degree angle on the side of the finger with the probe on a horizontal plane with that of the fingernail.

Desirably, software running on the computer system is programmed to assist an operator during data acquisition. For example, the screen may display a visual anatomical schematic having a highlighted interrogation point overlay that helps the device operator identify and place the interrogation probe. The screen image desirably changes as required to inform the operator of the desired interrogation point for each point of interest during a data acquisition series. A user-perceptible output, such as a low level modulated tone, may be produced to provide real-time feedback to the device operator to verify completion of an acceptable measurement. The conductance measurement profile for each conductance measurement may be displayed visually on the monitor. In use of a currently preferred device, the conductance value is sampled 25 times per second during each conductivity measurement.

Further, it is currently preferred for a computer-applied algorithm to control probe pressure to insure accurate and consistent measurements. Thus, the pressure applied to the skin surface during operation of the probe is reproducible and independent of operator force. The computer desirably implements threshold curves during electrode tip contact that adjust probe pressure in real-time to assure accurate readings and to prevent erroneous readings. After the measurement session is completed, the computer system may store the data for post processing.

A representative plot of a data-set obtained during time-based measurement of conductivity at an interrogation point is presented in FIG. 1. The x axis represents time and the y axis represents measured Conductivity Index. Conductivity Index is defined as measured conductance equivalent to resistance from 1K ohms to 999K ohms at a nominal 1.2 or 2.4 volts. Firmware in the device holds a current of approximately 10 microAmps, measures the voltage and then calculates the conductance. The software/firmware of computer system desirably employs an algorithm that increases a specified amount of probe pressure. The algorithm then commands constant probe pressure and monitors measurement stability for a period of time, such as for 5 seconds. Electrical conductivity is measured between the interrogation electrode and reference electrode during a time interval as a data-set, and this information is passed to the computer system. The measured conductance is plotted as the Conductivity Index normalized on a scale of 0 to 100.

Nine attributes may be parsed from a data-set illustrated in the graph of FIG. 1, which describe certain portions of such plot are defined as follows:

Base Max (max) is the maximum conductivity index value after zero slope is attained.

Base Min (min) is the minimum conductivity index value after zero slope is attained.

Base Rise (rise) is the angle between the starting conductivity index and the conductivity index at zero slope.

Base Fall (fall) is the angle between the conductivity index at the zero slope point and the conductivity index at the end of measurement.

Base Drop (drop) is the difference between the Base Max and the Base Min.

Area under the curve prior to zero slope (auca) is the area under the curve from start to zero slope.

Area under the curve after zero slope (aucb) is the area under the curve representing the the portion of the curve during last 5 seconds from zero slope to end of measurement.

Area under the curve total (auctotal) is the percentage of the area under the curve from start of measurement to end of measurement.

Total Samples (totalsamp) is the total number of measurements of the curve taken.

Acceptability of measurements may be determined by the system, and the clinician may receive perceptible feedback from the computer system to confirm satisfactory completion of a data collection operation. Factors that may be evaluated to determine if data is collected successfully include: 1) Rise in conductivity to a zero slope, computer control; 2) Continued signal measurement thru the sustain timeout value without unexpected fluctuations, computer control and operator control; 3) If the blue line indicating zero slope doesn't appear within the first 2 seconds, the measurement should be repeated, operator control; 4) Excessive drop values greater than 3 repeated to confirm, operator control. Failed measurements include: 1) Premature zero slope—machine control; 2) Excessive rise or drop after zero slope—machine control; 3) Low conductivity measurement as first measure especially if no other low conductivity measurements—operator control re-measure if max is below 10; 4) No probe reset at first contact—operator control.

Figure 3:
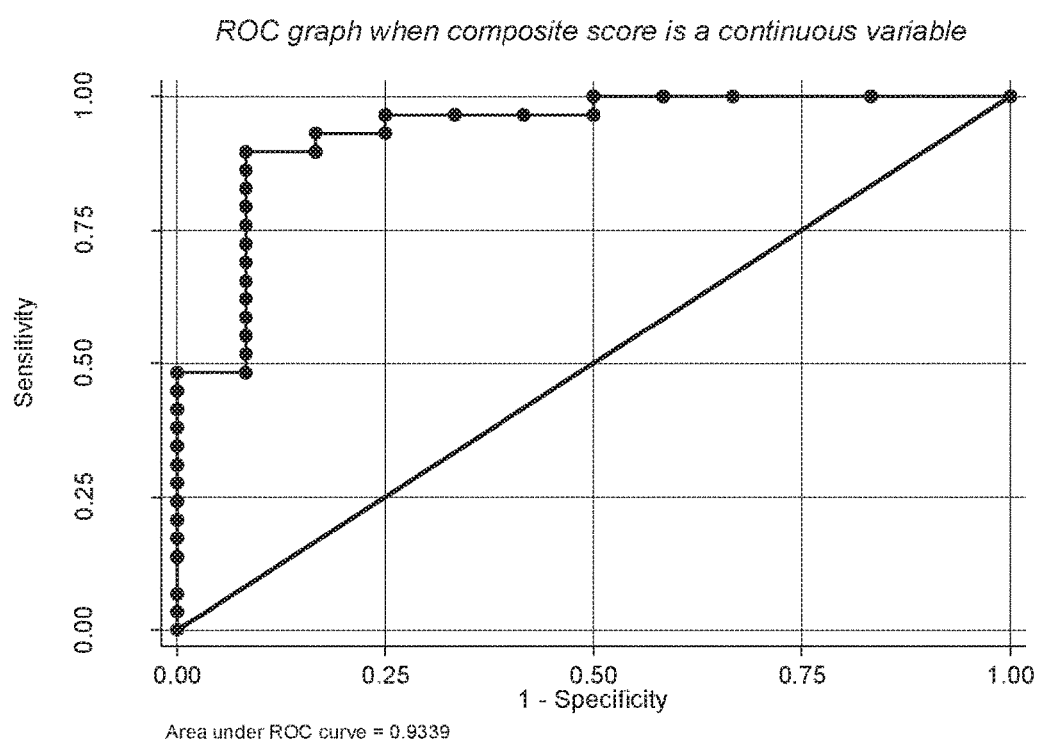
FIG. 3 is a ROC graph when the composite score is a continuous variable.

FIG. 3 is a flow chart that describes an operable method to determine a rule-set for point-attribute data effective to diagnosis a disease condition in a patient. A rule-set including point-attribute threshold criteria may be determined by obtaining conductivity data-sets at one or more points on the body of each subject from two arm groups of sample subjects. One arm group should be diagnosed as having the disease, and the other group should be free of the disease. Conductivity measurements may be made blind to knowledge of the subject arm group. The conductivity data can be expanded to a plurality of point-attributes for consideration of predictive capability with visibility to arm group. Accuracy, or predictive capacity, for each point-attribute may be determined by comparing "disease" data to "disease-free" data. A composite score may be developed from relevant point-attribute information.

Figure 2:
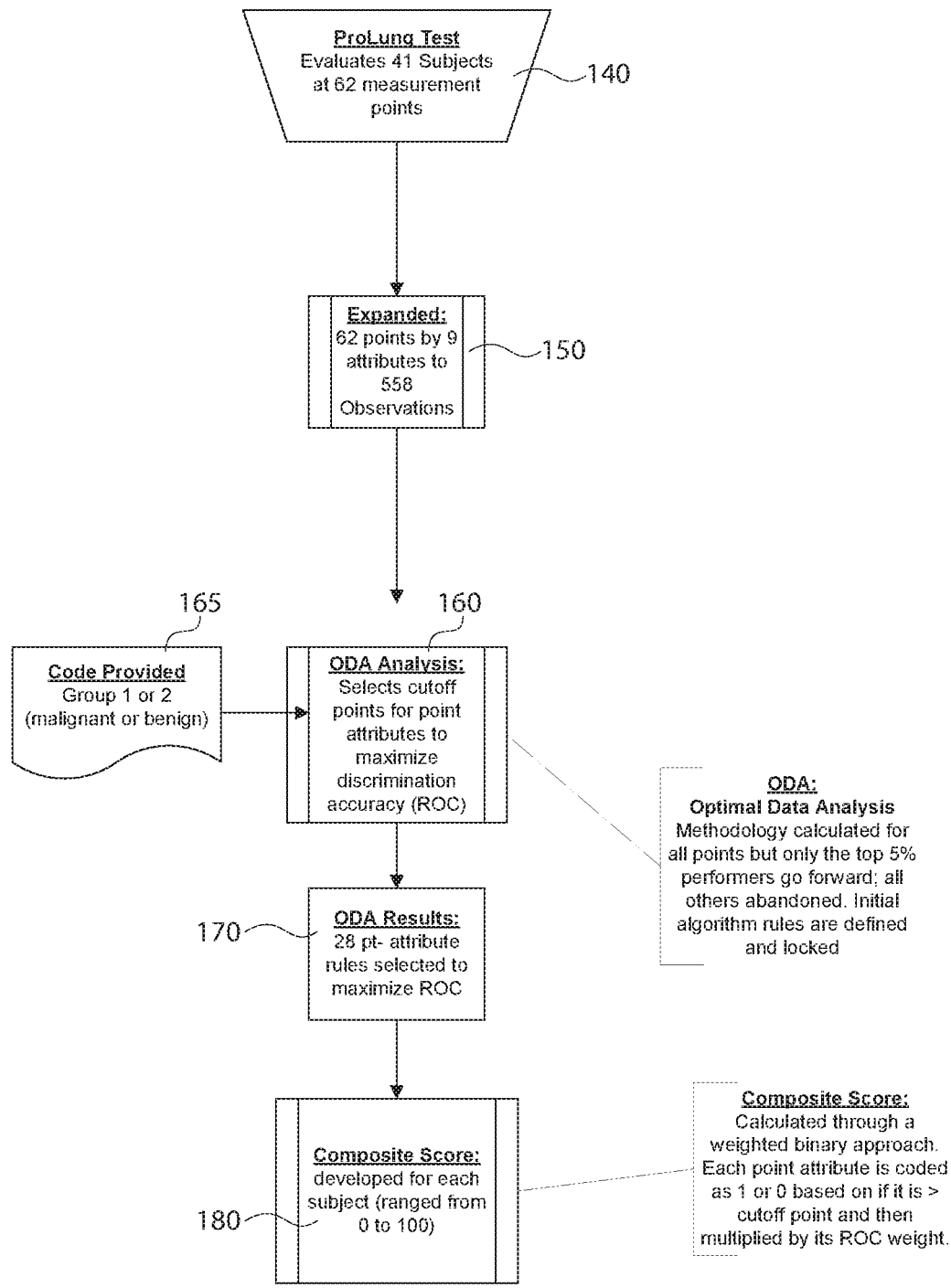
FIG. 2 is a flow chart illustrating a methodology to determine predictive rules including a disease-side bias.

With reference to the flow chart shown in FIG. 2, time-based conductivity measurements for 41 subjects are taken at 62 points on the patient's skin and reference points on each patient, as indicated at 140, for 9 different attributes. Measurements are blind to subject's group membership. At 150, the obtained data is expanded to 558 point-attributes (62 points measured×9 different attributes for each point=558 point attributes).

Lung cancer often exhibits a side-bias, with dominant presence on one side (lung) of the body. Therefore, data analysis can include a determination of disease-sidedness based upon conductivity values. The data analysis presented in FIG. 2 includes all 558 point-attributes, representing points located bilaterally, with 31 on the left side and 31 on the right side of the body.

At 165, the blind is removed and Optimal Data Analysis (ODA) is performed at 160. ODA is a tool that evaluates the discrimination capability of all point attribute combinations. Overall ODA accuracy is the fraction of cases a point attribute combination correctly determined as malignant or benign. At 170, it is determined that threshold values exist for 28 point-attributes that satisfy a threshold criteria of greater than about 70% accuracy for indicating presence of lung cancer. The cutoff at 0.70 was arbitrary—no clinical importance was associated with this cutoff. Either a higher or a lower overall ODA accuracy criteria could have been used.

A z-score is one way to adjust factors to make them of equal weight. For example, Base Max ranges from 0 to 100 and AUC total ranges from 0 to 1. If a Base Max score is to be combined with an AUC total score and each have an equal weight, z-scores are used. The z-score is calculated by taking the weighted average of the values. The composite score is developed by adding each z-score multiplied by total accuracy and dividing by the sum of all of the weights.

A composite score for each subject is calculated using z-scores as indicated at 180. With reference to FIG. 2, those point attribute combinations that have accuracy above the selected value are then combined. A confidence level may be determined.

In general, low conductivity suggests the presence of cancer. The "direction of low conductivity" set forth in Table 1, below, indicates whether low or high values of the evaluated point-attribute indicate cancer or low conductivity. This is obvious for most point attributes, but not obvious for base drop.

The present invention provides methods to effectively discriminate between having a malignant lung lesion and not having a malignant lung lesion in a medical patient. In one aspect, the methods comprise the steps of providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient, and measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values. The methods further comprise the step of comparing a plurality of curve attribute values obtained from the at least one patient data set to a plurality of corresponding curve attribute values in a previously-determined corresponding data set obtained using a similar measuring step. In some embodiments, the previously-determined corresponding data set is determined by comparing, from a population of patients having lung lesions, (i) a first cohort having malignant lung lesions and (ii) a second cohort not having malignant lung lesions, the malignant lung lesions of the previously-determined corresponding data set being determined by examination of lesion biopsies, to obtain a data set that effectively discriminates between the cohort having the malignant lung lesion and the cohort not having a malignant lung lesion, to thereby determine the likelihood of the patient having a malignant lung lesion.

In some embodiments of the invention, the at least one value in a previously-determined corresponding data set comprises a threshold value indicative of a likelihood of the patient having a malignant lesion. In other embodiments, the previously determined data set provides threshold values for a plurality of point-attributes that satisfy a threshold criteria of ROC area sufficient to discriminate between a patient having a malignant lung lesion and a patient not having a malignant lung lesion. In still other embodiments, the threshold values for the plurality of point-attributes satisfy a threshold criteria of greater than about 70% ROC area for discriminating between a patient having a malignant lung lesion and a patient not having a malignant lung lesion.

In another aspect, in the methods of the present invention, the previously determined corresponding data set is derived from a population of patients having lung lesions located in a similar region of the lung as the lesion in the patient. In some embodiments, the lung lesion of the patient is present in a lung location selected from one or more of the right lobe (RL) and the left lobe (LL), and the previously determined corresponding data set is obtained from a cohort having malignant lung lesions and a cohort having benign lung lesions in a similar region of the lung. In some embodiments, the lung lesion of the patient is present in a lung location selected from one or more of the right lower lobe (RLL), right middle lobe (RML), right upper lobe (RUL), left lower lobe (LLL), and left upper lobe (LUL), and the previously determined corresponding data set is obtained from a cohort having malignant lung lesions and a cohort having benign lung lesions in a similar region of the lung.

In accordance with the present invention, it has been determined that there is significantly greater clinical value in discriminating between small malignant lesions and small non-malignant lesions. As described in the experimental section below, it has surprisingly been discovered that bioconductance methods of the present invention, when applied to a patient population stratified on the basis of lung lesion size, may provide improved ability to discriminate between malignant and non-malignant lesions. In some embodiments, the lung lesion of the patient is of a size similar to the size of the lung lesions used to obtain the previously determined corresponding data set. In yet other embodiments, the lung lesions of the patient and the lung lesions used to obtain the previously determined corresponding data set range in size from 0 to about 15 mm, about 16 to about 30 mm, or from about 31 mm or greater. In other embodiments, the lung lesions of the patient and the lung lesions used to obtain the previously determined corresponding data set differ in size by no greater than about 2 mm, 5 mm, 10 mm, or 15 mm.

In another aspect of the invention, the point-attribute values comprise the total number of points measured to form the curve. In some embodiments, the point attribute values comprise an area under the curve (AUC) measurement calculated by measuring the area under the curve of a plot of the conductivity index over time of a curve segment from the point at which the slope of the curve is stable. In other embodiments, the point attribute values comprise an area under the curve (AUC) measurement calculated by measuring the area under the curve of a plot of the conductivity index over time of a curve segment from the point at which the slope of the curve is stable, wherein the duration of the curve segment comprises at least 5 seconds. In yet other embodiments, the point attribute values further comprise an area under the curve (AUC) measurement calculated by measuring the area under the curve of a plot of the conductivity index over time of a curve segment comprising the last 5 seconds of the curve.

In another aspect, the point-attribute values comprise an area under the curve (AUC) measurement calculated by measuring the height of the curve at selected intervals and summing said heights. In some embodiments, the height of the curve is calculated at intervals of about 25× per second.

In some aspects, the methods comprise developing a composite score for a patient indicative of a likelihood of the patient having lung cancer. In other aspects, the methods comprise a composite score that is developed by converting a subset of obtained point-attribute values to corresponding z-scores, and combining the z-scores.

In another aspect, the present invention relates to methods to effectively discriminate between having a malignant lung lesion and not having a malignant lung lesion in a medical patient, comprising:
  providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;
  measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;
  comparing a plurality of curve attribute values obtained from the at least one patient data set to a plurality of corresponding curve attribute values in a previously-determined corresponding data set obtained using a similar measuring step, wherein at least one of the curve attribute values is the total number of points measured to form the curve;
  wherein the previously-determined corresponding data set was determined by comparing, from a population of patients having lung lesions, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

In another aspect, the present invention relates to methods to effectively discriminate between having a malignant lung lesion and not having a malignant lung lesion in a medical patient, comprising:

providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;

measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;

comparing a plurality of curve attribute values obtained from the at least one patient data set to a plurality of corresponding curve attribute values in a previously-determined corresponding data set obtained using a similar measuring step;

wherein the previously-determined corresponding data set was determined by comparing, from a population of patients having lung lesions located in a similar region of the lung as the lesion of the patient, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

In some embodiments, the lung lesion of the patient is present in a region of the lung selected from one or more of the right lobe (RL) and the left lobe (LL), and the previously determined corresponding data set is obtained from a cohort having malignant lung lesions and a cohort having benign lung lesions in the same lung location. In some embodiments, the lung lesion of the patient is present in a region of the lung selected from one or more of the right lower lobe (RLL), right middle lobe (RML), right upper lobe (RUL), left lower lobe (LLL), and left upper lobe (LUL), and the previously determined corresponding data set is obtained from a cohort having malignant lung lesions and a cohort having benign lung lesions in the same lung location.

In another aspect, the present invention relates to a method to effectively discriminate between having a malignant lung lesion and not having a malignant lung lesion in a medical patient, comprising:

providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;

measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;

comparing a plurality of curve attribute values obtained from the at least one patient data set to a plurality of corresponding curve attribute values in a previously-determined corresponding data set obtained using a similar measuring step;

wherein the previously-determined corresponding data set was determined by comparing, from a population of patients having lung lesions of similar size as the lung lesion of the patient, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

In another aspect, the present invention relates to a method to effectively discriminate between having a malignant lung lesion and not having a malignant lung lesion in a medical patient, comprising:

providing a measurement device operable to measure conductivity between a reference point and an interrogation point on the body of a medical patient having an indeterminate lung lesion, wherein the measurement device is configured to provide control of contact pressure between a measurement electrode tip and the surface of the body of the patient;

measuring the conductivity between a plurality of reference points and a plurality of interrogation points with the measurement device by administering sufficient pressure between the measurement electrode tip and the surface of the body of the patient until a plot of a conductivity index over time exhibits a slope at or near zero, to obtain at least one patient data set comprising a plurality of conductivity curves having a plurality of curve attribute values;

comparing a plurality of curve attribute values obtained from the at least one patient data set to a plurality of corresponding curve attribute values in a previously-determined corresponding data set obtained using a similar measuring step, wherein the point attribute values comprise an area under the curve (AUC) measurement calculated by measuring the area under the curve of a plot of the conductivity index over time of a curve segment from the point at which the slope of the curve is stable;

wherein the previously-determined corresponding data set was determined by comparing, from a population of patients having lung lesions, (i) a first cohort having malignant lung lesions and (ii) a second cohort not having malignant lung lesions, to obtain a data set that effectively discriminates between the first cohort having a malignant lung lesion and the second cohort not having a malignant lung lesion, to thereby determine the likelihood of the patient having a malignant lung lesion.

EXPERIMENTAL RESULTS

Several trials were conducted, as described below, to determine whether discriminatory power can be improved.

Trial 1—Improved Discrimination Using Total Samples and Stable AUC Curve Measurements A single-center, single-arm trial was conducted to evaluate the utility of the bioconductance scan platform as adjunctive to CT scan in the diagnosis of lung cancer, as described below. The approach taken was to select "between subjects" optimal cut-points separately for each point-attribute that maximizes the ROC Area, and then combined the top 5% of these into a composite score. The usefulness of a bioconductance device is based on observations that electrical impedance, or bioconductivity may have utility in the prediction of the presence of cancerous tissue. It has been discovered that low conductivity measurements taken non-invasively at the skin are indications of lung disease, specifically lung cancer.

Points or Measurement Locations

For each patient, the device was used to measure bioconductivity between 62 locations on the surface of the skin and reference points on each patient. These points are located bilaterally, with 31 on the left side and 31 on the right side of body. The locations of these measurements are at specific anatomical locations on the skin surface, as described in detail above.

Attributes

Each of the 62 measurements was used to generate a bioconductance curve (as illustrated in FIG. 2), with each curve being characterized by 9 different attributes pertaining to certain segments or characteristics of each curve. Conductivity is reflected in each attribute as either a high or low value based upon the following:

TABLE 1

| Attribute | Attribute short name | Direction of Attribute Measurement: (low/high) value correlates with low conductivity |
|---|---|---|
| Base Min | min | low |
| Base Max | max | low |
| AUC prior to zero slope | auca | low |
| AUC after zero slope | aucb | low |
| AUC total | auctotal | low |
| Total Samples | totalsamp | low |
| Base Rise | rise | low |
| Base Fall | fall | high |
| Base Drop | drop | high |

Approach for Deriving Composite Score Predictive of Low Conductivity (Malignancy)

There are 62 total points, each measured or characterized based upon the above 9 attributes, for a total of 62×9=558 candidate variables. Those variables most indicative of low conductivity, using one variable at a time, are selected to be included in a final composite score. This final composite score represents a prediction equation.

An Optimal Data Analysis (ODA) approach was used to identify which point-attribute combinations were the most predictive. ODA is a statistical approach for classifying groups on an attribute, or variable. For a given variable, it finds the optimal cut-point for classifying two groups (if cut-point, classify into one group; if >cut-point, classify into the other group). The cut-point that provides the best test characteristic is considered the optimal cut-point. [Yarnold, P R, Soltysik R C. *Optimal Data Analysis: A Guidebook With Software for Windows*. Washington D.C., Amercan Psychological Association, 2005.]

The analysis was performed using the statistical software Stata release 11 [College Station, Tex.: StataCorp LP, 2009]. The Stata routine was programmed to find the optimal cut-point that maximized the receiver operating characteristic (ROC) area separately for each variable. This routine was validated by comparing the result from several test variables to that provided by Yarnold and Soltysik's ODA software.

The top 5% of the variables, or point-attribute combinations, were combined into a composite score using the "weighted binary approach" described below under the Composite Score (Prediction Equation) subheading. In that section, the rule is described and demonstrated using the actual data. The optimal cut-point for the composite score, that maximized ROC area, was then used to define a binary diagnostic decision criterion (positive for malignancy, negative for malignancy) and test characteristics computed to assess the predictive accuracy in terms familiar to clinicians (sensitivity, specificity, and ROC area).

A variety of test characteristics could be used in ODA as indices of discriminatory ability. The six test characteristics are as follows:

| | ODA Prediction | | |
|---|---|---|---|
| True Status (reference standard) | Malignant defined By cut-point | Non-malignant defined by cut-point | row total |
| malignant | a | b | a + b |
| non-malignant | c | d | c + d |
| column total | a + c | b + d | N = a + b + c + d |

Accuracy=(# correct classifications)/(# classifications made)=(a+d)/N

Sensitivity=proportion true positives=a/(a+b)=proportion of times predicted to have a malignancy when patient actually has one Specificity=proportion true negatives=d/(c+d)=proportion of times predicted to not have a malignancy when patient actually does not have one Positive predictive value (PPV)=(# malignant)/(# predicted malignant)=a/(a+c)=proportion of times patient has malignancy when predicted to have one [not used: see note below]

Negative predictive value (NPV)=(# not malignant)/(# predicted not malignant)=d/(b+d)=proportion of times patients does not have malignancy when predicted to not have one

[not used: see note below]

ROC area=(sensitivity+specificity)/2, once data reduced to a 2×2 table [Cantor S B, Kattan M W. Determining the area under the ROC curve for a binary diagnostic test. *Med Decis Making* 2000; 20:468-470.]

For this report, to optimize discrimination, the point-attribute combinations that have the ROC area were used. The point-attributes with the top 5% of ROC area values were then used to form a composite score.

Results (Top 5% ROC area)

For the N=558 point-attribute combinations, the ROC areas were observed at their optimal cut-points, as set forth in the following table.

| ROC area | Freq. | Percent | Cum. | |
|---|---|---|---|---|
| 50 | 39 | 6.99 | 6.99 | |
| 50.57 | 1 | 0.18 | 7.17 | |
| ... | | | | |
| 68.53 | 5 | 0.90 | 90.14 | |
| 68.97 | 3 | 0.54 | 90.68 | |
| 69.25 | 2 | 0.36 | 91.04 | |
| 69.54 | 3 | 0.54 | 91.58 | |
| 69.97 | 4 | 0.72 | 92.29 | |
| 70.26 | 3 | 0.54 | 92.83 | |
| 70.55 | 2 | 0.36 | 93.19 | |
| 70.98 | 8 | 1.43 | 94.62 | |
| 71.26 | 1 | 0.18 | 94.80 | |
| 71.55 | 1 | 0.18 | 94.98 | |
| 71.7 | 3 | 0.54 | 95.52 | top performers (n = 28) |
| 72.27 | 5 | 0.90 | 96.42 | ≥95th percentile |
| 72.7 | 2 | 0.36 | 96.77 | top 5.0% |
| 72.99 | 2 | 0.36 | 97.13 | |
| 73.42 | 5 | 0.90 | 98.03 | |
| 73.71 | 1 | 0.18 | 98.21 | |
| 75.14 | 4 | 0.72 | 98.92 | |
| 76.44 | 1 | 0.18 | 99.10 | |
| 76.87 | 3 | 0.54 | 99.64 | |
| 77.87 | 1 | 0.18 | 99.82 | |
| 82.04 | 1 | 0.18 | 100.00 | |
| Total | 558 | 100.00 | | |

The top 28 (top 5%) performers (had highest ROC area) are as follows.

| pointid | attribute | maxrocarea | cut-pointroc |
|---|---|---|---|
| 1. FML-12bR | drop | 82.04 | 1 |
| 2. FML-12cR | auca | 72.99 | 2796 |
| 3. FML-12cR | aucb | 72.27 | 8303 |
| 4. FML-12cR | auctotal | 76.44 | 11441 |
| 5. FML-12cR | max | 72.99 | 65 |
| 6. FML-12cR | min | 72.27 | 65 |
| 7. FML-1L | aucb | 72.27 | 9732 |

-continued

| pointid | attribute | maxrocarea | cut-pointroc |
|---|---|---|---|
| 8. FML-1L | max | 72.27 | 78 |
| 9. FML-1L | min | 72.27 | 78 |
| 10. FML-1aTR | auca | 76.87 | 1652 |
| 11. FML-1aTR | aucb | 75.14 | 4380 |
| 12. FML-1aTR | auctotal | 76.87 | 6439 |
| 13. FML-1aTR | max | 75.14 | 37 |
| 14. FML-1aTR | min | 75.14 | 37 |
| 15. FML-1aTR | totalsamp | 75.14 | 172 |
| 16. FML-1bTR | auca | 76.87 | 1474 |
| 17. FML-1bTR | aucb | 73.42 | 4311 |
| 18. FML-1bTR | auctotal | 73.42 | 5570 |
| 19. FML-1bTR | max | 73.42 | 35 |

-continued

| pointid | attribute | maxrocarea | cut-pointroc |
|---|---|---|---|
| 20. FML-1bTR | min | 73.42 | 35 |
| 21. FML-1bTR | totalsamp | 73.71 | 181 |
| 22. FML-1cTL | aucb | 71.7 | 3900 |
| 23. FML-1cTL | max | 71.7 | 32 |
| 24. FML-1cTL | min | 71.7 | 32 |
| 25. FML-2aL | auca | 73.42 | 7826 |
| 26. FML-3aL | auca | 77.87 | 3431 |
| 27. FML-6aR | totalsamp | 72.7 | 193 |
| 28. FML-7cL | totalsamp | 72.7 | 182 |

Composite Score (Prediction Equation)

The top 28 most discriminatory point-attribute combinations, as assessed by ROC area, were combined into a composite score using a variety of approaches. One such approach is a weighted binary approach, as follows. Each of the 28 measurements is recoded into 1 or 0, defined by each measurement cut-point (1 if below cut-point, 0 if above, and opposite for fall and drop). A composite score was then computed as the weighted average of the 28 binary variables, using the ROC areas as the weights.

Using the top 28 performers identified in the above table, composite scores were computed for each patient, using the following algorithm:

$$\text{Composite Score} = (1 \text{ if } FML\text{-}12bR \text{ drop} \geq 1, 0 \text{ otherwise}) \times (0.8204) +$$
$$(1 \text{ if } FML\text{-}12cR \text{ auca} \leq 2796, 0 \text{ otherwise}) \times (0.7299) \ldots +$$
$$(1 \text{ if } FML\text{-}7cL \text{ totalsamp} \leq 182, 0 \text{ otherwise}) \times$$
$$(0.7270)/(0.8204 + 0.7299 + \ldots + 0.7270)$$

As shown in the following table, a two-sample t-test was computed on the composite score, comparing the group having malignant tumors with the group not having malignant tumors.

| Two-sample T Test With Equal Variances | | | | | | |
|---|---|---|---|---|---|---|
| Group | Obs | Mean | Std. Err. | Std. Dev. | [95% Conf. Interval] | |
| 0 | 12 | .1700052 | .0627194 | .2172662 | .0319608 | .3080496 |
| 1 | 29 | .6495415 | .0516906 | .2783625 | .5436581 | .755425 |
| combined | 41 | .5091894 | .0531947 | .3406121 | .401679 | .6166999 |
| diff | | −.4795363 | .0901267 | | −.6618347 | −.297238 | diff = mean(0) − mean(1)   t = −5.3207
Ho: diff = 0   degrees of freedom = 39
Ha: diff < 0   Ha: diff != 0   Ha: diff > 0
Pr(T < t) = 0.0000   Pr(|T| > |t|) = 0.0000   Pr(T > t) = 1.0000
two-tailed p value Adjusting the p Value for Multiplicity In deriving this composite score, multiplicity arises from the multiple point-attributes, the multiple possible cutpoints for each one, and the multiple ways to arrive at the top 5% best performers. The situation is somewhat analogous to genome-wide association studies, where there are millions of markers, each with its own significance test. For those studies, a Bonferroni correction is applied, so that a marker is not determined to be significant unless p<10e-8. Taking the same approach as genome-wide association studies, alpha was set at 10e-8 to protect against a false positive conclusion (Type I error) (where <alpha=10e-8=0.00000010=1 in 10 million chance). Using the Stata software, the t=−5.3207, with 39 degrees of freedom, has a p value of 9.571e-8, which is smaller than alpha=10e-8, so it is concluded the composite score was statistically significant, with the malignant group having a higher composite score 0.48 higher on average than the benign group.

As shown in the following table, the composite score was cross tabulated with the actual malignancy status reference standard, and the maximum ROC area=90.7 was achieved at cut-point 0.29.

| | malignant | | |
|---|---|---|---|
| Composite | 0 | 1 | Total |
| 0 | 2 | 0 | 2 | |
| .0346646 | 2 | 0 | 2 | |
| .0349078 | 1 | 0 | 1 | |
| .0697059 | 1 | 0 | 1 | |
| .1086714 | 0 | 1 | 1 | |
| .1452814 | 1 | 0 | 1 | Test decision: benign |
| .2137333 | 1 | 0 | 1 | (3 false negatives) |
| .2168946 | 1 | 0 | 1 | |
| .2174191 | 0 | 1 | 1 | |
| .2208712 | 1 | 0 | 1 | |
| .2534903 | 0 | 1 | 1 | |
| .2864431 | 1 | 0 | 1 | |
| ---------- | | | | ----optimal cut-point |
| .2918836 | 0 | 1 | 1 | (highest ROC area) |
| .2949353 | 0 | 1 | 1 | |
| .3255422 | 0 | 1 | 1 | |
| .3599874 | 0 | 1 | 1 | |
| .4299937 | 0 | 1 | 1 | Test decision: malignant |
| .4321441 | 0 | 1 | 1 | (1 false positive) |
| .4339704 | 0 | 1 | 1 | |
| .4351624 | 0 | 1 | 1 | |
| .578012 | 0 | 1 | 1 | |
| .7115971 | 0 | 1 | 1 | |
| .7460853 | 0 | 1 | 1 | |
| .748684 | 0 | 1 | 1 | |
| .7828956 | 1 | 0 | 1 | |
| .7866577 | 0 | 1 | 1 | |
| .7908394 | 0 | 1 | 1 | |
| .8196821 | 0 | 1 | 1 | |
| .8208884 | 0 | 1 | 1 | |
| .8217801 | 0 | 1 | 1 | |
| .8914096 | 0 | 1 | 1 | |
| .8956295 | 0 | 1 | 1 | |
| .9292928 | 0 | 1 | 1 | |
| .9299651 | 0 | 1 | 1 | |
| .9304562 | 0 | 1 | 1 | |
| .9611155 | 0 | 2 | 2 | |
| .9651209 | 0 | 1 | 1 | |
| .9651733 | 0 | 1 | 1 | |
| Total | 12 | 29 | 41 | |

At the cut-point≥0.29, ROC area is maximized at 90.7%. The 2×2 test diagnostic test table (maximizing on ROC area) is as follows:

| | Composite Score | | |
|---|---|---|---|
| True Status (referent standard) | Malignant ≥0.29 | Benign <0.29 | row total |
| malignant | 26 true positive | 3 false negative | 29 |
| benign | 1 false positive | 11 true negative | 12 |
| column total | 27 | 14 | 41 |

Sensitivity=26/29=89.7%
Specificity=11/12=91.7%
ROC Area=(sensitivity+specificity)/2=(89.7+91.7)/2=90.7%
PPV and NPV are not shown, since are biased estimates with the case-control study design that was used Interpreting ROC Hosmer D W and Lemeshow S. (*Applied Logistic Regression.* 2$^{nd}$ ed. New York, John Wiley & Sons, 2000, p. 162) apply the following general rule for interpreting the area under the ROC curve:

ROC=0.5 suggests no discrimination (i.e., no better than flipping a coin)

0.7≤ROC<0.8 is considered acceptable discrimination 0.8≤ROC<0.9 is considered excellent discrimination ROC≥0.9 is considered outstanding discrimination (extremely unusual to observe this in practice)

Figure 4:
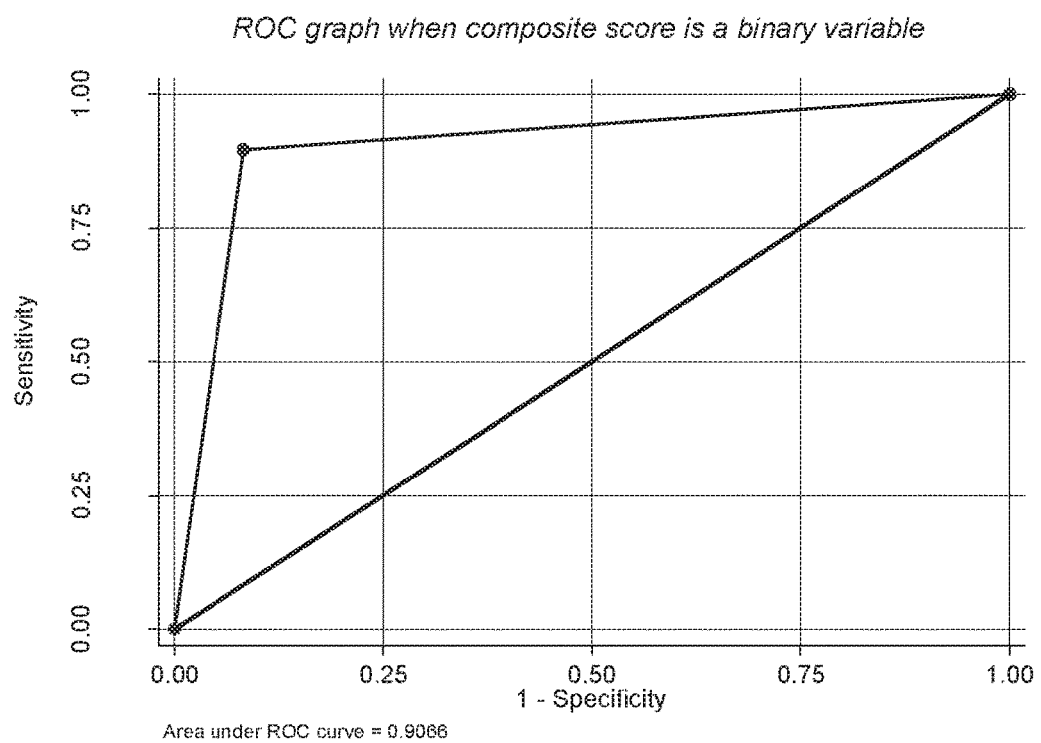
FIG. 4 is a ROC graph when the composite score is a binary variable.

FIG. 4 shows a ROC graph when the composite score is a continuous variable.

FIG. 5 shows a ROC graph when the composite score is a binary value (matching the 2×2 table above). A list of subject IDs with composite scores (1=malignant, 0=benign) are shown in the following table.

| subjectid | composite | malignant | |
|---|---|---|---|
| 1. FML-204-002 | 0 | 0 | |
| 2. FML-204-028 | 0 | 0 | |
| 3. FML-204-011 | .0346646 | 0 | |
| 4. FML-204-034 | .0346646 | 0 | |
| 5. FML-204-042 | .0349078 | 0 | |
| 6. FML-204-041 | .0697059 | 0 | |
| 7. FML-204-020 | .1086714 | 1 | false negative |
| 8. FML-204-050 | .1452814 | 0 | |
| 9. FML-204-054 | .2137333 | 0 | |
| 10. FML-204-035 | .2168946 | 0 | |
| 11. FML-204-024 | .2174191 | 1 | false negative |
| 12. FML-204-009 | .2208712 | 0 | |
| 13. FML-204-023 | .2534903 | 1 | false negative |
| 14. FML-204-012 | .2864431 | 0 | |
| ---------- | | | ----Cut-point |
| 15. FML-204-018 | .2918836 | 1 | |
| 16. FML-204-019 | .2949353 | 1 | |
| 17. FML-204-016 | .3255422 | 1 | |
| 18. FML-204-038 | .3599874 | 1 | |
| 19. FML-204-025 | .4299937 | 1 | |
| 20. FML-204-049 | .4321441 | 1 | |
| 21. FML-204-030 | .4339704 | 1 | |
| 22. FML-204-033 | .4351624 | 1 | |
| 23. FML-204-027 | .578012 | 1 | |
| 24. FML-204-031 | .7115971 | 1 | |
| 25. FML-204-044 | .7460853 | 1 | |
| 26. FML-204-003 | .748684 | 1 | |
| 27. FML-204-052 | .7828956 | 0 | false positive |
| 28. FML-204-029 | .7866577 | 1 | |
| 29. FML-204-037 | .7908394 | 1 | |
| 30. FML-204-047 | .8196821 | 1 | |
| 31. FML-204-017 | .8208884 | 1 | |
| 32. FML-204-051 | .8217801 | 1 | |
| 33. FML-204-036 | .8914096 | 1 | |
| 34. FML-204-045 | .8956295 | 1 | |
| 35. FML-204-007 | .9292928 | 1 | |
| 36. FML-204-021 | .9299651 | 1 | |
| 37. FML-204-005 | .9304562 | 1 | |
| 38. FML-204-022 | .9611155 | 1 | |
| 39. FML-204-013 | .9611155 | 1 | |
| 40. FML-204-055 | .9651209 | 1 | |
| 41. FML-204-006 | .9651733 | 1 | |

Based on the above composite scores, those patients having malignant tumors were correctly identified in all but one case (with false negatives in on three cases). This approach thus illustrates the high level of specificity and sensitivity, as well as the high discriminatory power, of the methodology.

Conclusion

On the basis of the above data, it was determined that bioconductance measurements can be successfully used to discriminate between patients having malignant lung tumors and patients not having malignant lung tumors. Moreover, it was determined that the additional point attribute of "Total Samples" significantly improved the ability to discriminate between patients having malignant lung tumors and patients not having malignant lung tumors. In addition, it was determined that calculating the AUC after zero slope from the region of the curve when the curve has stabilized (i.e., the last 5 seconds of the curve) also significantly improved the ability to discriminate between patients having malignant lung tumors and patients not having malignant lung tumors.

Trial 2—Discrimination on the Basis of Lesion Location

Another trial was conducted to determine whether patient stratification on the basis of lesion location within the lung can improve discrimination of malignant lesions and benign lesions. Six patients having malignant lesions in the right lower lobe were compared with 7 patients having benign lesions in the right lower lobe, right middle lobe and right upper lobe, as described in the following table.

| Subgroup | Malignant (N) | Benign (N) |
|---|---|---|
| RLL (mass on right lower lobe) | 6 | 1 |
| RML (mass on right middle lobe) |  | 1 |
| RUL (mass on right upper lobe) |  | 5 |

For the N=558 point-attribute combinations, the following ROC areas where observed at their optimal cut-points

| ROC area | Freq. | Percent | Cum. | |
|---|---|---|---|---|
| 50 | 96 | 17.20 | 17.20 | |
| 51.19 | 17 | 3.05 | 20.25 | |
| ... | | | | |
| 71.43 | 52 | 9.32 | 92.83 | |
| 75 | 8 | 1.43 | 94.27 | |
| 76.19 | 9 | 1.61 | 95.88 | top 5% performers |
| 77.38 | 3 | 0.54 | 96.42 | (n = 32) |
| 78.57 | 9 | 1.61 | 98.03 | |
| 83.33 | 4 | 0.72 | 98.75 | |
| 85.71 | 2 | 0.36 | 99.10 | |
| 91.67 | 4 | 0.72 | 99.82 | |
| 92.86 | 1 | 0.18 | 100.00 | |
| Total | 558 | 100.00 | | |

The top 32 (top 5%) performers (had highest ROC area) were as follows:

| pointid | attribute | maxrocarea | cutpointroc |
|---|---|---|---|
| 1. FML-11bL | rise | 85.71 | 26 |
| 2. FML-12cR | auca | 78.57 | 2796 |
| 3. FML-12cR | totalsamp | 83.33 | 162 |
| 4. FML-1L | auca | 85.71 | 3600 |
| 5. FML-1L | auctotal | 78.57 | 13552 |
| 6. FML-1aTR | aucb | 76.19 | 5329 |
| 7. FML-1aTR | max | 76.19 | 45 |
| 8. FML-1aTR | min | 76.19 | 45 |
| 9. FML-1aTR | totalsamp | 76.19 | 168 |
| 10. FML-1bTL | rise | 83.33 | 16 |
| 11. FML-1cTL | rise | 76.19 | 13 |
| 12. FML-1cTR | rise | 91.67 | 18 |
| 13. FML-2aL | aucb | 91.67 | 7826 |
| 14. FML-2aL | auctotal | 83.33 | 9318 |
| 15. FML-2aL | max | 91.67 | 63 |
| 16. FML-2aL | min | 91.67 | 63 |
| 17. FML-2aR | auca | 78.57 | 3819 |
| 18. FML-2aR | aucb | 76.19 | 8004 |
| 19. FML-2aR | max | 76.19 | 65 |
| 20. FML-2aR | min | 76.19 | 65 |
| 21. FML-3aL | auca | 92.86 | 3431 |
| 22. FML-3aL | auctotal | 77.38 | 12512 |
| 23. FML-4L | rise | 83.33 | 19 |
| 24. FML-4R | aucb | 76.19 | 7287 |
| 25. FML-4R | auctotal | 77.38 | 10778 |
| 26. FML-5L | auctotal | 78.57 | 12370 |
| 27. FML-6aL | rise | 78.57 | 24 |
| 28. FML-6aR | totalsamp | 77.38 | 195 |
| 29. FML-6dL | auca | 78.57 | 3582 |
| 30. FML-6dL | aucb | 78.57 | 9375 |
| 31. FML-6dL | max | 78.57 | 75 |
| 32. FML-6dL | min | 78.57 | 75 |

Cross-tabulating the composite score with the actual malignancy status (reference standard), the maximum ROC area=100% is achieved at cutpoint 0.602.

| | malignant | | | |
|---|---|---|---|---|
| Composite | 0 | 1 | Total | |
| 0 | 1 | 0 | 1 | |
| .0303446 | 1 | 0 | 1 | Test decision: benign |
| .0602296 | 1 | 0 | 1 | (0 false negatives) |
| .0933317 | 1 | 0 | 1 | |
| .2726416 | 1 | 0 | 1 | |
| .4289643 | 1 | 0 | 1 | |
| .5462024 | 1 | 0 | 1 | |
| | | | | optimal cut-point |
| .6027591 | 0 | 1 | 1 | (highest ROC area) |
| .638163 | 0 | 1 | 1 | |
| .8294223 | 0 | 1 | 1 | |
| .9411492 | 0 | 1 | 1 | Test decision: malignant |
| .970115 | 0 | 1 | 1 | (0 false positive) |
| 1 | 0 | 1 | 1 | |
| Total | 7 | 6 | 13 | |

The 2×2 test diagnostic test table (maximizing on ROC area) is as follows:

| | Composite Score | | |
|---|---|---|---|
| True Status (referent standard) | Malignant ≥0.602 | Benign <0.602 | row total |
| malignant | 6 true positive | 0 false negative | 6 |
| benign | 0 false positive | 7 true negative | 7 |
| column total | 6 | 7 | 13 |

Sensitivity=6/6=100%
Specificity=7/7=100%
ROC Area=(sensitivity+specificity)/2=(100+100)/2=100%

The listing of subject IDs with composite score (1=malignant, 0=benign) is shown in the following table:

| subjectid | composite | malignant |
|---|---|---|
| 1. FML-204-028 | 0 | 0 |
| 2. FML-204-042 | .03034458 | 0 |
| 3. FML-204-011 | .06022956 | 0 |
| 4. FML-204-012 | .09333169 | 0 |
| 5. FML-204-035 | .2726416 | 0 |
| 6. FML-204-054 | .42896426 | 0 |

| subjectid | composite | malignant |
|---|---|---|
| 7. FML-204-052 | .54620239 | 0 |
| --- | --- | cutpoint |
| 8. FML-204-033 | .60275909 | 1 |
| 9. FML-204-016 | .63816303 | 1 |
| 10. FML-204-036 | .82942231 | 1 |
| 11. FML-204-038 | .94114921 | 1 |
| 12. FML-204-031 | .97011501 | 1 |
| 13. FML-204-013 | 1 | 1 |

Based on the above composite scores, those patients having malignant tumors were correctly identified in all cases.

Conclusion

The above results demonstrate that the methods described herein can be applied to patient groups stratified on the basis of lesion location in the lung, with improved discriminatory power.

Trial 3—Discrimination on the Basis of Lesion Location

Another trial was conducted to determine whether patient stratification on the basis of lesion location within the lung can improve discrimination of malignant lesions and benign lesions. Three patients having malignant lesions in the right middle lobe were compared with 7 patients having benign lesions in the right lower lobe, right middle lobe and right upper lobe, as described in the following table.

| Subgroup | Malignant (N) | Benign (N) |
|---|---|---|
| RLL (mass on right lower lobe) | | 1 |
| RML (mass on right middle lobe) | 3 | 1 |
| RUL (mass on right upper lobe) | | 5 |

For the N=558 point-attribute combinations, the following ROC areas where observed at their optimal cut-points.

| maxrocarea | Freq. | Percent | Cum. | |
|---|---|---|---|---|
| 50 | 113 | 20.25 | 20.25 | |
| 52.38 | 11 | 1.97 | 22.22 | |
| 54.76 | 20 | 3.58 | 25.81 | |
| 57.14 | 48 | 8.60 | 34.41 | |
| 59.52 | 33 | 5.91 | 40.32 | |
| 61.9 | 44 | 7.89 | 48.21 | |
| 64.29 | 93 | 16.67 | 64.87 | |
| 66.67 | 24 | 4.30 | 69.18 | |
| 69.05 | 42 | 7.53 | 76.70 | |
| 71.43 | 75 | 13.44 | 90.14 | |
| 76.19 | 10 | 1.79 | 91.94 | |
| 78.57 | 30 | 5.38 | 97.31 | top 5% performers |
| 83.33 | 3 | 0.54 | 97.85 | (n = 45) |
| 85.71 | 8 | 1.43 | 99.28 | |
| 92.86 | 2 | 0.36 | 99.64 | |
| 100 | 2 | 0.36 | 100.00 | |
| Total | 558 | 100.00 | | |

The above results show perfect discrimination for two points.

The top 45 (top 8.1%) performers (had highest ROC area) were as follows:

| pointid | attribute | maxrocarea | cutpointroc |
|---|---|---|---|
| 1. FML-10L | rise | 92.86 | 21 |
| 2. FML-12aL | aucb | 78.57 | 8316 |
| 3. FML-12aL | auctotal | 78.57 | 11534 |
| 4. FML-12aL | max | 78.57 | 67 |
| 5. FML-12aL | min | 78.57 | 65 |
| 6. FML-12aR | aucb | 78.57 | 8738 |
| 7. FML-12aR | auctotal | 78.57 | 12225 |
| 8. FML-12bL | drop | 78.57 | 1 |
| 9. FML-12bR | drop | 83.33 | 1 |
| 10. FML-12cR | aucb | 78.57 | 7734 |
| 11. FML-12cR | auctotal | 78.57 | 10517 |
| 12. FML-12cR | drop | 78.57 | 1 |
| 13. FML-12cR | max | 78.57 | 62 |
| 14. FML-12cR | min | 78.57 | 61 |
| 15. FML-1L | auca | 78.57 | 4014 |
| 16. FML-1L | auctotal | 78.57 | 13712 |
| 17. FML-1R | rise | 85.71 | 26 |
| 18. FML-1aTR | rise | 83.33 | 13 |
| 19. FML-1bTL | aucb | 85.71 | 5350 |
| 20. FML-1bTL | auctotal | 78.57 | 7441 |
| 21. FML-1bTL | max | 85.71 | 44 |
| 22. FML-1bTL | min | 85.71 | 44 |
| 23. FML-1bTL | rise | 83.33 | 14 |
| 24. FML-1bTR | rise | 85.71 | 15 |
| 25. FML-1cTL | rise | 92.86 | 16 |
| 26. FML-1cTR | rise | 100 | 17 |
| 27. FML-2aR | auca | 78.57 | 3074 |
| 28. FML-2cL | rise | 78.57 | 28 |
| 29. FML-6aL | rise | 85.71 | 20 |
| 30. FML-7aL | aucb | 85.71 | 8113 |
| 31. FML-7aL | min | 85.71 | 62 |
| 32. FML-7aR | rise | 100 | 24 |
| 33. FML-7cR | auca | 78.57 | 3389 |
| 34. FML-7cR | aucb | 78.57 | 8625 |
| 35. FML-7cR | auctotal | 78.57 | 11490 |
| 36. FML-7cR | max | 78.57 | 69 |
| 37. FML-8bL | rise | 78.57 | 23 |
| 38. FML-8cL | auca | 78.57 | 3222 |
| 39. FML-8cL | aucb | 78.57 | 7875 |
| 40. FML-8cL | auctotal | 78.57 | 11097 |
| 41. FML-8cL | max | 78.57 | 63 |
| 42. FML-8cL | min | 78.57 | 63 |
| 43. FML-8cR | auctotal | 78.57 | 10235 |
| 44. FML-8fR | drop | 78.57 | 2 |
| 45. FML-8fR | fall | 78.57 | 2 |

Cross-tabulating the composite score with the actual malignancy status (reference standard), the maximum ROC area=100% is achieved at cutpoint 0.977

| | malignant | | | |
|---|---|---|---|---|
| Composite | 0 | 1 | Total | |
| .0213593 | 1 | 0 | 1 | |
| .0640779 | 1 | 0 | 1 | Test decision: benign |
| .1922338 | 1 | 0 | 1 | (0 false negatives) |
| .2155341 | 1 | 0 | 1 | |
| .4854356 | 1 | 0 | 1 | |
| .6271867 | 1 | 0 | 1 | |
| .7398036 | 1 | 0 | 1 | |
| --- | | | | optimal cut-point |
| .9773467 | 0 | 1 | 1 | (highest ROC area) |
| .9773467 | 0 | 2 | 2 | Test decision: malignant |
| | | | | (0 false positive) |
| Total | 7 | 3 | 10 | |

The 2×2 test diagnostic test table (maximizing on ROC area) is as follows:

| True Status (referent standard) | Composite Score Malignant ≥0.977 | Benign <0.977 | row total |
|---|---|---|---|
| malignant | 3 true positive | 0 false negative | 3 |
| benign | 0 false positive | 7 true negative | 7 |
| column total | 3 | 7 | 10 |

Sensitivity=3/3=100%
Specificity=7/7=100%
ROC Area=(sensitivity+specificity)/2=(100+100)/2=100%

The following table provides a listing of subject IDs with composite score (1=malignant, 0=benign)

| subjectid | composite | malignant |
|---|---|---|
| 1. FML-204-042 | .02135931 | 0 |
| 2. FML-204-028 | .06407792 | 0 |
| 3. FML-204-012 | .19223377 | 0 |
| 4. FML-204-011 | .21553409 | 0 |
| 5. FML-204-054 | .4854356 | 0 |
| 6. FML-204-035 | .6271867 | 0 |
| 7. FML-204-052 | .73980356 | 0 |
| --- | --- cutpoint | --- |
| 8. FML-204-023 | .97734668 | 1 |
| 9. FML-204-019 | .97734668 | 1 |
| 10. FML-204-017 | .97734668 | 1 |

Based on the above composite scores, those patients having malignant tumors were correctly identified in all cases.

Conclusion

The above results demonstrate that the methods described herein can be applied to patient groups stratified on the basis of lesion location in the lung.

Trial 4—Discrimination on the Basis of Small (0-15 Mm) Lesion Size

Another trial was conducted to determine whether patient stratification on the basis of lesion size can improve discrimination of malignant lesions and benign lesions. Six patients having malignant lesions in the in the size range of 0-15 mm masses were compared with 5 patients having benign lesions in the same size range, as described in the following table.

| Subgroup | Malignant (N) | Benign (N) |
|---|---|---|
| Small [0-1.5 cm (0-15 mm) mass] | 6 | 5 |

For the N=558 point-attribute combinations, the following ROC areas where observed at their optimal cut-points

| maxrocarea | Freq. | Percent | Cum. |
|---|---|---|---|
| 50 | 98 | 17.56 | 17.56 |
| 51.67 | 10 | 1.79 | 19.35 |
| 53.33 | 3 | 0.54 | 19.89 |
| 55 | 13 | 2.33 | 22.22 |
| 56.67 | 9 | 1.61 | 23.84 |
| 58.33 | 49 | 8.78 | 32.62 |
| 60 | 47 | 8.42 | 41.04 |
| 61.67 | 30 | 5.38 | 46.42 |

-continued

| maxrocarea | Freq. | Percent | Cum. | |
|---|---|---|---|---|
| 63.33 | 27 | 4.84 | 51.25 | |
| 65 | 44 | 7.89 | 59.14 | |
| 66.67 | 43 | 7.71 | 66.85 | |
| 70 | 29 | 5.20 | 72.04 | |
| 71.67 | 22 | 3.94 | 75.99 | |
| 73.33 | 33 | 5.91 | 81.90 | |
| 75 | 46 | 8.24 | 90.14 | |
| 80 | 17 | 3.05 | 93.19 | |
| 81.67 | 23 | 4.12 | 97.31 | top 5% performers (n = 43) |
| 83.33 | 13 | 2.33 | 99.64 | |
| 90 | 1 | 0.18 | 99.82 | |
| 91.67 | 1 | 0.18 | 100.00 | |
| Total | 558 | 100.00 | | |

The top 38 (top 6.8%) performers (had highest ROC area) were:

| | pointid | attribute | maxrocarea | cutpointroc |
|---|---|---|---|---|
| 1. | FML-12bL | auctotal | 83.33 | 9763 |
| 2. | FML-12bR | auctotal | 83.33 | 10201 |
| 3. | FML-12bR | rise | 83.33 | 26 |
| 4. | FML-12cL | auca | 83.33 | 1942 |
| 5. | FML-12cR | auca | 83.33 | 1912 |
| 6. | FML-1L | aucb | 81.67 | 9858 |
| 7. | FML-1L | max | 81.67 | 79 |
| 8. | FML-1L | min | 81.67 | 79 |
| 9. | FML-1R | auctotal | 81.67 | 13664 |
| 10. | FML-1cTR | rise | 81.67 | 22 |
| 11. | FML-2aR | auctotal | 81.67 | 12497 |
| 12. | FML-2cR | aucb | 81.67 | 9060 |
| 13. | FML-2cR | max | 81.67 | 74 |
| 14. | FML-2cR | min | 81.67 | 74 |
| 15. | FML-3aL | auctotal | 81.67 | 12539 |
| 16. | FML-3aR | totalsamp | 81.67 | 202 |
| 17. | FML-3bL | auctotal | 81.67 | 13271 |
| 18. | FML-4R | rise | 81.67 | 22 |
| 19. | FML-5L | auctotal | 81.67 | 12370 |
| 20. | FML-5L | max | 81.67 | 71 |
| 21. | FML-5L | min | 81.67 | 71 |
| 22. | FML-5R | auctotal | 81.67 | 13793 |
| 23. | FML-5R | totalsamp | 90 | 209 |
| 24. | FML-7bL | rise | 81.67 | 26 |
| 25. | FML-8aR | aucb | 83.33 | 8500 |
| 26. | FML-8aR | max | 83.33 | 68 |
| 27. | FML-8aR | rise | 83.33 | 24 |
| 28. | FML-8bR | auca | 81.67 | 2892 |
| 29. | FML-8bR | aucb | 83.33 | 8000 |
| 30. | FML-8bR | auctotal | 81.67 | 10788 |
| 31. | FML-8bR | max | 83.33 | 64 |
| 32. | FML-8cL | rise | 81.67 | 26 |
| 33. | FML-8dL | auca | 83.33 | 2974 |
| 34. | FML-8dL | totalsamp | 83.33 | 182 |
| 35. | FML-8eL | totalsamp | 81.67 | 183 |
| 36. | FML-8eR | totalsamp | 83.33 | 178 |
| 37. | FML-8fL | auca | 81.67 | 2359 |
| 38. | FML-8fL | totalsamp | 91.67 | 181 |

Crosstabulating the composite score with the actual malignancy status (referent standard), the maximum ROC area=100% is achieved at cutpoint 0.579

| | malignant | | | |
|---|---|---|---|---|
| composite | 0 | 1 | Total | |
| 0 | 1 | 0 | 1 | Test decision: benign |
| .0519633 | 1 | 0 | 1 | (0 false negatives) |
| .0519633 | 1 | 0 | 1 | |
| .1065767 | 1 | 0 | 1 | |
| .4157067 | 1 | 0 | 1 | |

-continued

| | malignant | | | |
|---|---|---|---|---|
| composite | 0 | 1 | Total | |
| | | | | optimal cut-point |
| .5795404 | 0 | 1 | 1 | (highest ROC area) |
| .7364866 | 0 | 1 | 1 | |
| .7863249 | 0 | 1 | 1 | Test decision: malignant |
| .8176002 | 0 | 1 | 1 | (0 false positive) |
| .8430538 | 0 | 1 | 1 | |
| .9209988 | 0 | 1 | 1 | |
| Total | 5 | 6 | 11 | |

The 2×2 test diagnostic test table (maximizing on ROC area) is:

| | Composite Score | | |
|---|---|---|---|
| True Status (referent standard) | Malignant ≥0.579 | Benign <0.579 | row total |
| malignant | 6 true positive | 0 false negative | 6 |
| benign | 0 false positive | 5 true negative | 5 |
| column total | 6 | 5 | 11 |

Sensitivity=6/6=100%

Specificity=5/5=100%

ROC Area=(sensitivity+specificity)/2=(100+100)/2=100%

Listing of Subject IDs with Composite Score (1=Malignant, 0=Benign)

| | subjectid | composite | malignant |
|---|---|---|---|
| 1. | FML-204-009 | 0 | 0 |
| 2. | FML-204-042 | .05196334 | 0 |
| 3. | FML-204-034 | .05196334 | 0 |
| 4. | FML-204-012 | .1065767 | 0 |
| 5. | FML-204-054 | .41570671 | 0 |
| | | | cutpoint |
| 6. | FML-204-018 | .57954043 | 1 |
| 7. | FML-204-019 | .73648664 | 1 |
| 8. | FML-204-013 | .78632487 | 1 |
| 9. | FML-204-016 | .81760022 | 1 |
| 10. | FML-204-051 | .84305379 | 1 |
| 11. | FML-204-029 | .9209988 | 1 |

Based on the above composite scores, those patients having malignant tumors were correctly identified in all cases.

Conclusion

The above results demonstrate that the methods described herein can be applied to patient groups stratified on the basis of tumor size.

Trial 5—Discrimination on the Basis of Medium (16-30 Mm) Lesion Size

Another trial was conducted to determine whether patient stratification on the basis of lesion size can improve discrimination of malignant lesions and benign lesions. Seven patients having malignant lesions in the size range of 16-30 mm masses were compared with 4 patients having benign lesions in the same size range, as described in the following table.

| Subgroup | Malignant (N) | Benign (N) |
|---|---|---|
| Moderate [1.6 cm-3 cm (16-30 mm) mass] | 8* (7) | 4 |

*1 of these is bilateral, so dropped leaving 7

For the N=558 point-attribute combinations, the following ROC areas where observed at their optimal cut-points.

| maxrocarea | Freq. | Percent | Cum. | |
|---|---|---|---|---|
| 50 | 112 | 20.07 | 20.07 | |
| 51.79 | 8 | 1.43 | 21.51 | |
| 53.57 | 13 | 2.33 | 23.84 | |
| 55.36 | 21 | 3.76 | 27.60 | |
| 57.14 | 39 | 6.99 | 34.59 | |
| 58.93 | 31 | 5.56 | 40.14 | |
| 60.71 | 17 | 3.05 | 43.19 | |
| 62.5 | 68 | 12.19 | 55.38 | |
| 64.29 | 37 | 6.63 | 62.01 | |
| 66.07 | 42 | 7.53 | 69.53 | |
| 67.86 | 25 | 4.48 | 74.01 | |
| 71.43 | 37 | 6.63 | 80.65 | |
| 73.21 | 33 | 5.91 | 86.56 | |
| 75 | 14 | 2.51 | 89.07 | |
| 78.57 | 28 | 5.02 | 94.09 | |
| 80.36 | 11 | 1.97 | 96.06 | top 5% performers (n = 33) |
| 85.71 | 17 | 3.05 | 99.10 | |
| 87.5 | 3 | 0.54 | 99.64 | |
| 92.86 | 1 | 0.18 | 99.82 | |
| 100 | 1 | 0.18 | 100.00 | |
| Total | 558 | 100.00 | | |

The top 33 (top 5.9%) performers (had highest ROC area) were as follows:

| | pointid | attribute | maxrocarea | cutpointroc |
|---|---|---|---|---|
| 1. | FML-10R | rise | 85.71 | 22 |
| 2. | FML-12cR | auca | 87.5 | 2966 |
| 3. | FML-12cR | auctotal | 87.5 | 11708 |
| 4. | FML-12cR | max | 80.36 | 65 |
| 5. | FML-1L | aucb | 85.71 | 8316 |
| 6. | FML-1bTR | totalsamp | 80.36 | 185 |
| 7. | FML-2aR | auca | 87.5 | 3074 |
| 8. | FML-2aR | aucb | 85.71 | 7083 |
| 9. | FML-2aR | auctotal | 85.71 | 9407 |
| 10. | FML-2aR | max | 85.71 | 57 |
| 11. | FML-2aR | min | 85.71 | 57 |
| 12. | FML-2aTL | aucb | 85.71 | 2489 |
| 13. | FML-2aTL | auctotal | 85.71 | 3407 |
| 14. | FML-2aTL | max | 85.71 | 22 |
| 15. | FML-2aTL | min | 85.71 | 22 |
| 16. | FML-2bR | auca | 85.71 | 2629 |
| 17. | FML-2bR | totalsamp | 80.36 | 208 |
| 18. | FML-3aL | auca | 80.36 | 3410 |
| 19. | FML-3bR | auctotal | 85.71 | 11333 |
| 20. | FML-5L | auca | 80.36 | 3544 |
| 21. | FML-5R | totalsamp | 85.71 | 212 |
| 22. | FML-6aL | aucb | 80.36 | 8146 |
| 23. | FML-6aL | max | 80.36 | 66 |
| 24. | FML-6aL | min | 80.36 | 66 |
| 25. | FML-6aR | auca | 80.36 | 3155 |
| 26. | FML-6aR | totalsamp | 100 | 197 |
| 27. | FML-6dL | auca | 85.71 | 2688 |
| 28. | FML-6dL | auctotal | 80.36 | 10920 |
| 29. | FML-6dL | totalsamp | 92.86 | 194 |
| 30. | FML-6eL | auca | 85.71 | 1936 |
| 31. | FML-7cL | totalsamp | 85.71 | 178 |
| 32. | FML-8cL | totalsamp | 85.71 | 179 |
| 33. | FML-8fL | rise | 80.36 | 32 |

Crosstabulating the composite score with the actual malignancy status (referent standard), the maximum ROC area=100% is achieved at cutpoint 0.361

| | malignant | | | |
|---|---|---|---|---|
| composite | 0 | 1 | Total | |
| .0287371 | 2 | 0 | 2 | Test decision: benign |
| .0287371 | 1 | 0 | 1 | (0 false negatives) |
| .3237674 | 1 | 0 | 1 | |
| --------- | --- | --- | --- | optimal cut-point |
| .361441 | 0 | 1 | 1 | (highest ROC area) |
| .7011504 | 0 | 1 | 1 | |
| .8180118 | 0 | 1 | 1 | |
| .8773991 | 0 | 1 | 1 | |
| .9099625 | 0 | 1 | 1 | Test decision: malignant |
| .9693498 | 0 | 1 | 1 | (0 false positive) |
| .9712629 | 0 | 1 | 1 | |
| Total | 4 | 7 | 11 | |

The 2×2 test diagnostic test table (maximizing on ROC area) is as follows:

| | Composite Score | | |
|---|---|---|---|
| True Status (referent standard) | Malignant ≥0.361 | Benign <0.361 | row total |
| malignant | 7 true positive | 0 false negative | 7 |
| benign | 0 false positive | 4 true negative | 4 |
| column total | 7 | 4 | 11 |

Sensitivity=7/7=100%
Specificity=4/4=100%
ROC Area=(sensitivity+specificity)/2=(100+100)/2=100%
Listing of Subject IDs with Composite Score (1=Malignant, 0=Benign)

| | subjectid | composite | malignant |
|---|---|---|---|
| 1. | FML-204-050 | .02873705 | 0 |
| 2. | FML-204-002 | .02873705 | 0 |
| 3. | FML-204-041 | .02873705 | 0 |
| 4. | FML-204-052 | .32376743 | 0 |
| --- | --- | --- | cutpoint |
| 5. | FML-204-023 | .361441 | 1 |
| 6. | FML-204-038 | .70115041 | 1 |
| 7. | FML-204-036 | .81801179 | 1 |
| 8. | FML-204-025 | .87739908 | 1 |
| 9. | FML-204-031 | .90996249 | 1 |
| 10. | FML-204-007 | .96934977 | 1 |
| 11. | FML-204-021 | .97126295 | 1 |

Based on the above composite scores, those patients having malignant tumors were correctly identified in all cases.

Conclusion

The above results demonstrate that it is further possible to apply the methods described herein to patient groups stratified on the basis of a larger tumor size.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A computer-implemented method to effectively discriminate between having conductance curve attributes associated with a malignant lung lesion and not having conductance curve attributes associated with a non-malignant lung lesion in a medical patient having a lung lesion of a particular size, comprising:

providing a measurement device, the measurement device comprising a computer assembly and a probe system comprising an interrogation electrode, the interrogation electrode comprising a motor and a probe tip operably coupled to the motor, the computer assembly comprising a processor, firmware, and memory in communication with a display device, the firmware configured to:

apply a current of a predefined value between a reference electrode and the interrogation electrode on a body of the medical patient having a lung lesion of indeterminate malignancy, the interrogation electrode configured to permit computer controlled application of electrode contact pressure onto the medical patient's skin during a measurement sequence in response to the motor operating on the probe tip;

measure a voltage as a function of the applied current;

calculate conductivity between the reference electrode and the interrogation electrode; and control an amount of contact pressure applied by the probe tip of the interrogation electrode on the medical patient's skin;

generating at least one patient data set, the patient data set comprising a plurality of conductivity curves generated by:

increasing, by a predefined amount over a plurality of time intervals until the slope of the conductivity curves is at or near zero, the contact pressure provided between the probe tip of the interrogation electrode and the medical patient's skin, holding the contact pressure constant for a predefined period of time after the contact pressure is increased for each time interval, measuring the conductivity between the interrogation and reference electrodes during the predefined period of time for each time interval, and normalizing the measured conductivity on a scale of 0 to 100, the conductivity curves having a plurality of curve attribute values, wherein each of the plurality of curve attribute values represents a conductivity value between the reference electrode and the interrogation electrode on the body of the medical patient;

selecting a previously-determined data set that corresponds to the at least one patient data set and comprises a plurality of conductivity measurements derived from a patient population comprising lung lesions, the previously-determined corresponding data set determined by comparing, from a population of patients having lung lesions located in a same region of the lung as the lesion of the medical patient, (i) a first cohort having malignant lung lesions and (ii) a second cohort not having malignant lung lesions, the malignant lung lesions of the previously-determined corresponding data set being determined by examination of lesion biopsies;

stratifying the previously-determined data set on the basis of lung lesion size, the stratified data set comprising a plurality of lung lesions that differ in size by no greater than 15 mm relative to the size of the lung lesion of the medical patient; and comparing the plurality of curve attribute values of the at least one patient data set to the plurality of corresponding curve attribute values of the stratified previously-determined data set to determine a likelihood of the medical patient having a malignant lung lesion.

2. The method of claim 1, wherein the at least one value in a previously-determined corresponding data set comprises a threshold value indicative of a likelihood of the patient having a malignant lesion.

3. The method of claim 1, wherein the previously determined data set provides threshold values for a plurality of point-attributes that satisfy a threshold criteria of ROC area that discriminate between a patient having a malignant lung lesion and a patient not having a malignant lung lesion.

4. The method of claim 3, wherein the point-attribute values comprise the total number of points measured to form the curve.

5. The method of claim 3, wherein the point attribute values comprise an area under the curve (AUC) measurement calculated by measuring the area under the curve of a plot of the conductivity index over time of a curve segment from the point at which the slope of the curve is stable.

6. The method of claim 1, wherein the curve values for a plurality of point-attributes satisfy a threshold criteria of greater than 70% ROC area for discriminating between a patient having a malignant lung lesion and a patient not having a malignant lung lesion.

7. The method of claim 1, wherein the lung lesion of the patient is present in a lung location selected from one or more of the right lobe (RL) and the left lobe (LL), and the previously determined corresponding data set is obtained from a cohort having malignant lung lesions and a cohort having benign lung lesions in a region of the lung.

8. The method of claim 1, wherein the lung lesions of the patient and the lung lesions used to obtain the previously determined corresponding data set range in size from greater than 0 to 15 mm.

9. The method of claim 1, further comprising developing a composite score for a patient indicative of a likelihood of the patient having lung cancer.

10. The method of claim 9, wherein the composite score is developed by converting a subset of obtained point-attribute values to corresponding z-scores, and combining the z-scores.

* * * * *